(12) United States Patent
Fujita et al.

(10) Patent No.: US 10,842,359 B2
(45) Date of Patent: Nov. 24, 2020

(54) CURVATURE SENSOR AND ENDOSCOPE APPARATUS EQUIPPED WITH THE SAME

(71) Applicant: OLYMPUS CORPORATION, Tokyo (JP)

(72) Inventors: Hiromasa Fujita, Hachioji (JP); Ken Sato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 402 days.

(21) Appl. No.: 15/825,179

(22) Filed: Nov. 29, 2017

(65) Prior Publication Data

US 2018/0084977 A1    Mar. 29, 2018

Related U.S. Application Data

(63) Continuation of application No. PCT/JP2015/065606, filed on May 29, 2015.

(51) Int. Cl.
*A61B 1/005* (2006.01)
*G02B 23/26* (2006.01)
(Continued)

(52) U.S. Cl.
CPC .......... *A61B 1/00165* (2013.01); *A61B 1/005* (2013.01); *A61B 1/0055* (2013.01);
(Continued)

(58) Field of Classification Search
CPC ............ A61B 1/00165; A61B 1/00167; A61B 1/0017; A61B 1/005; A61B 1/0055;
(Continued)

(56) References Cited

U.S. PATENT DOCUMENTS 5,633,494 A * 5/1997 Danisch ............. G02B 6/02057
250/227.14
6,612,992 B1 * 9/2003 Hossack ................. A61B 8/12
600/467

(Continued)

FOREIGN PATENT DOCUMENTS

| JP | 2007-249093 A | 9/2007 |
| WO | WO 2012/137846 A1 | 10/2012 |
| WO | WO 2015/019752 A1 | 2/2015 |

OTHER PUBLICATIONS

B.D. Gupta and R.K. Verma, "Surface Plasmon Resonance-Based Fiber Optic Sensors: Principle, Probe Designs, and Some Applications", 2009, Hindawi Publishing Corporation, Journal of Sensors, vol. 2009, pp. 1-12. (Year: 2009).*

(Continued)

*Primary Examiner* — John P Leubecker
(74) *Attorney, Agent, or Firm* — Scully, Scott, Murphy & Presser, P.C.

(57) ABSTRACT

Sensing parts are formed in different directions in a circumferential direction in substantially a same position in the longitudinal direction thereof. Each sensing part is configured to include an optical characteristic changing member which generates the optical signals having absorption wavelength characteristic regions that vary from sensing part to sensing part by giving an optical characteristic change, which differs from that of other sensing parts, to the sensor light incident thereon in accordance with an amount of bending in a specific direction. A light detector detects the optical signals included in sensor light from a light source, which has passed through the sensing parts and undergone the optical characteristic change.

19 Claims, 13 Drawing Sheets

(51) Int. Cl.
  *A61B 5/06* (2006.01)
  *A61B 1/00* (2006.01)
  *G01B 11/24* (2006.01)
  *G02B 6/14* (2006.01)
  *A61B 1/05* (2006.01)
  *G02B 23/24* (2006.01)

(52) U.S. Cl.
  CPC .......... *A61B 1/00071* (2013.01); *A61B 5/065* (2013.01); *G01B 11/24* (2013.01); *G02B 23/26* (2013.01); *A61B 1/00043* (2013.01); *A61B 1/05* (2013.01); *G02B 6/14* (2013.01); *G02B 23/24* (2013.01)

(58) Field of Classification Search
  CPC ............ A61B 5/065; A61B 2034/2061; A61B 2562/0266; G02B 11/24
  See application file for complete search history.

(56) References Cited

U.S. PATENT DOCUMENTS

| | | | | |
|---|---|---|---|---|
| 7,227,066 B1* | 6/2007 | Roscheisen | ......... | H01L 31/0296 117/94 |
| 7,440,661 B2 | 10/2008 | Kobayashi | | |
| 2002/0183592 A1* | 12/2002 | Suzuki | ............... | A61B 1/00071 600/145 |
| 2007/0116415 A1* | 5/2007 | Kobayashi | ............. | A61B 5/065 385/116 |
| 2011/0116743 A1* | 5/2011 | Arkwright | ............. | G02B 6/124 385/37 |
| 2013/0066228 A1* | 3/2013 | Capcelea | ............. | A61B 5/0084 600/559 |
| 2014/0036261 A1* | 2/2014 | Fujita | ..................... | G01B 11/18 356/300 |
| 2014/0328557 A1* | 11/2014 | Sakai | ................. | A61B 1/00165 385/12 |
| 2014/0332675 A1* | 11/2014 | Fujita | ..................... | G01B 11/16 250/227.16 |
| 2015/0100000 A1* | 4/2015 | Asaoka | ............. | A61B 1/00135 600/587 |
| 2017/0205256 A1* | 7/2017 | Kim | ........................ | G01J 1/04 |

OTHER PUBLICATIONS

English translation of International Preliminary Report on Patentability dated Dec. 14, 2017 together with the Written Opinion received in related International Application No. PCT/JP2015/065606.

International Search Report dated Aug. 25, 2015 issued in PCT/JP2015/065606.

\* cited by examiner

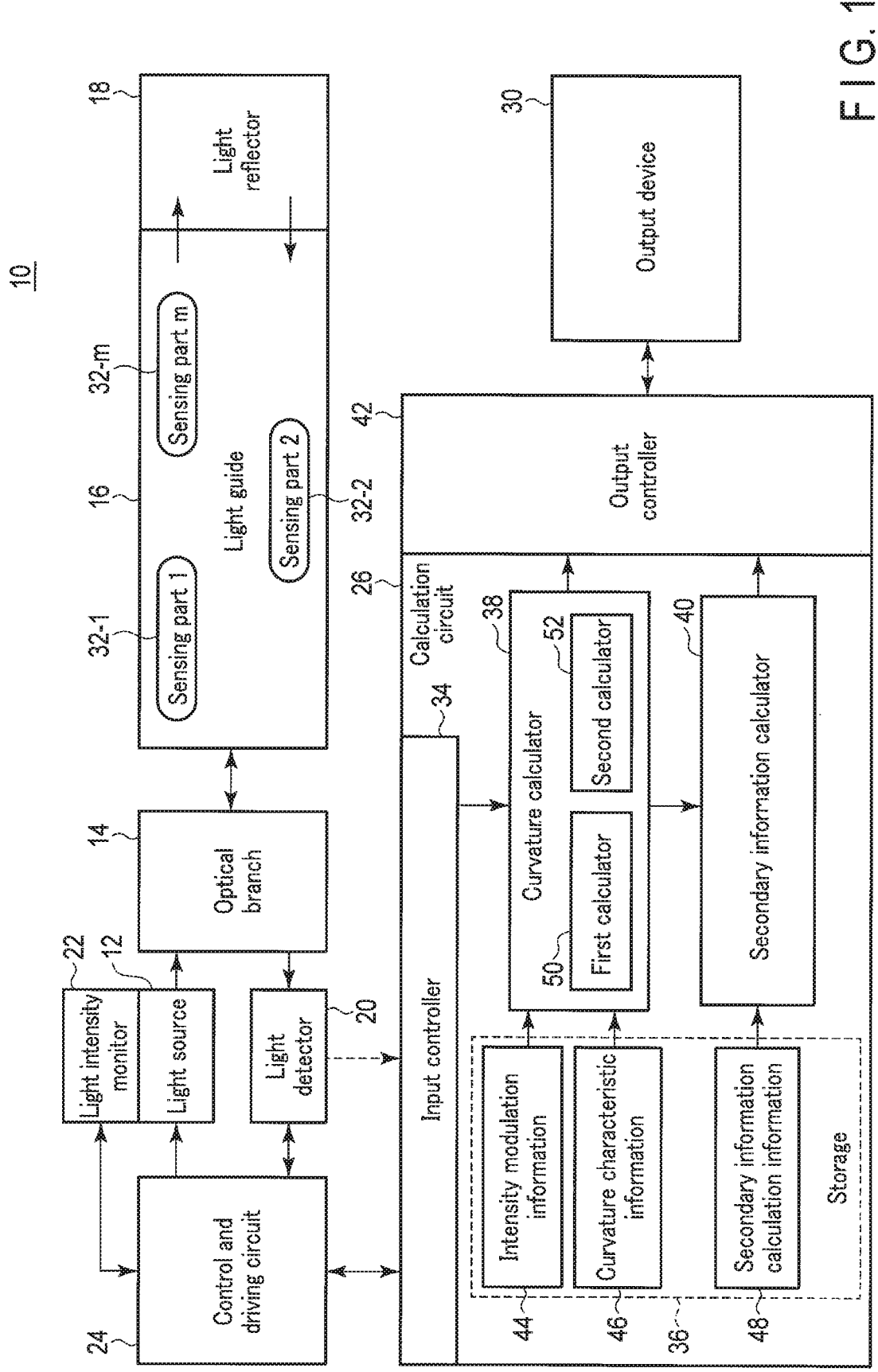
F I G. 1

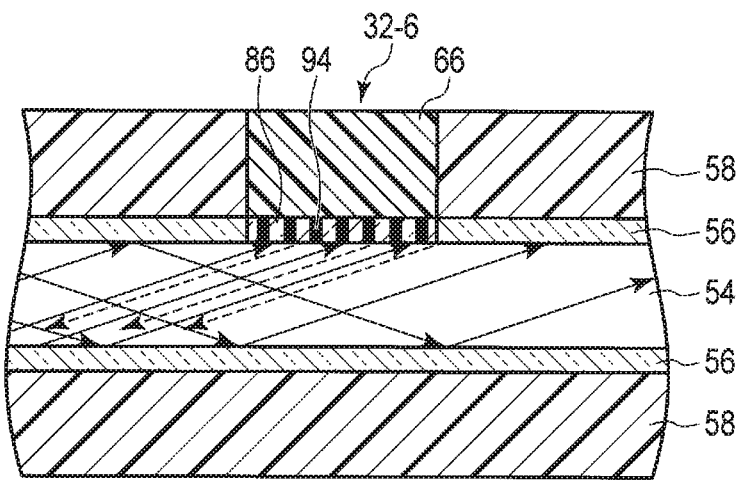
F I G. 16
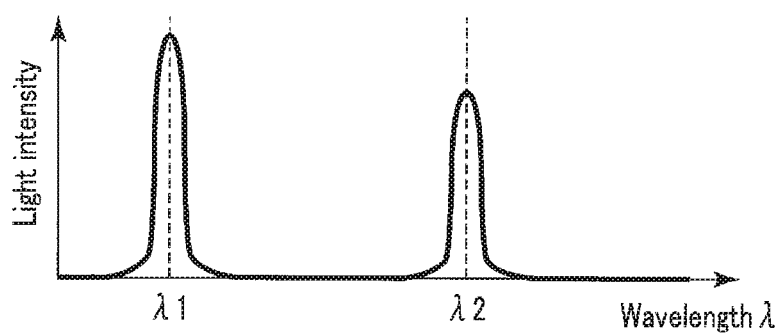
F I G. 17A
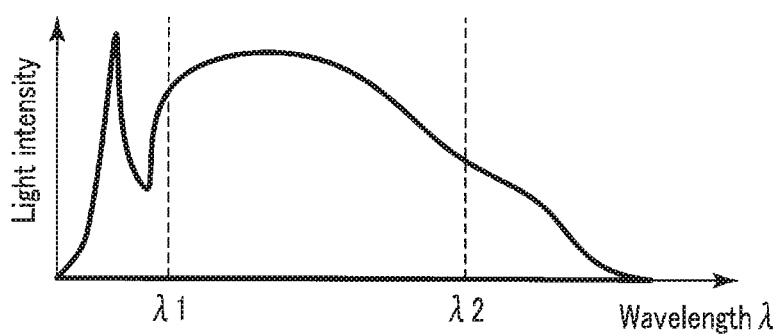
F I G. 17B

CURVATURE SENSOR AND ENDOSCOPE APPARATUS EQUIPPED WITH THE SAME

CROSS-REFERENCE TO RELATED APPLICATION

This application is a Continuation Application of PCT Application No. PCT/JP2015/065606, filed May 29 2015, the entire contents of which are incorporated herein by reference.

BACKGROUND OF THE INVENTION

1. Field of the Invention

The present invention relates to a curvature sensor for detecting a curvature of a sensing part with a flexible light guide and an endoscope apparatus equipped with the curvature sensor.

2. Description of the Related Art

U.S. Pat. No. 7,440,661 discloses an endoscope shape detection probe which is bent integrally with the scope of an endoscope as one unit and used to detect the shape of the scope.

The endoscope shape detection probe includes a curvature detecting fiber for transmitting detection light having different wavelength components and a light modulation unit provided in the curvature detecting fiber to modulate the intensity or wavelength of each of the different wavelength components of the detection light. The endoscope shape detection probe is characterized by allowing the shape of the scope to be detected based upon the intensity or wavelength of each of the wavelength components before and after the modulation by the light modulation unit serving as a sensing part, and the distance between the light modulation unit and the emission end of the curvature detecting fiber.

The U.S. Patent describes a configuration to absorb one of the different wavelength components as the light modulation unit, in which the curvature of one portion is detected using intensity modulation of light of a predetermined wavelength, wavelength modulation to absorb a predetermined wavelength and emit light of different wavelengths, etc. The endoscope shape detection probe of the U.S. Patent is characterized particularly in that the light modulation unit serving as a sensing part selectively absorbs one of the different wavelength components though the number of light modulation units is the same as the number of wavelength components included in the detection light.

BRIEF SUMMARY OF THE INVENTION

According to a first aspect of the present invention, there is provided a curvature sensor which detects curvature information from a plurality of optical signals derived from a plurality of sensing parts provided in a light guide having flexibility, the curvature sensor comprising: a light source which generates sensor light in emission wavelength regions including at least predetermined wavelength components; the light guide which has flexibility and confines and guides the sensor light; the sensing parts formed in at least one of (i) different positions in a longitudinal direction of the light guide and (ii) different directions in a circumferential direction in substantially a same position in the longitudinal direction thereof, and made of an elastic material, each of the sensing parts being configured to include an optical characteristic changing member which generates the optical signals having absorption wavelength characteristic regions that vary from sensing part to sensing part by changing optical characteristics of the sensor light guided by the light guide in accordance with an amount of bending of the light guide; and a light detector which detects the optical signals included in the sensor light from the light source, which has passed through the sensing parts and undergone the optical characteristic change, wherein the optical characteristic changing member is made of metal particles to absorb light in a predetermined wavelength region and has a special spectral absorption spectrum different from a spectral absorption spectrum peculiar to the metal, and the sensing parts are provided with optical characteristic changing members having different special spectral absorption spectra, and the special spectral absorption spectra of all the optical characteristic changing members at least overlap the emission wavelength region of the sensor light from the light source.

According to a second aspect of the present invention, there is provided an endoscope comprising: an insertion section which is a tubular insert to be insert into a subject that is an observation target; and the curvature sensor according to the first aspect of the present invention in which the light guide is disposed along the insertion section.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing a schematic configuration of a curvature sensor according to an embodiment of the present invention.

FIG. 16 is a cross-sectional view of the light guide, showing a configuration example of a sensing part using a grating.

FIG. 17A is a diagram showing a relationship between a spectrum of light from a light source emitting a discrete light and absorption wavelength characteristic regions.

FIG. 17B is a diagram showing a relationship between a spectrum of light from a light source emitting light of a continuous wavelength spectrum and absorption wavelength characteristic regions.

DETAILED DESCRIPTION OF THE INVENTION

Figure 2A:
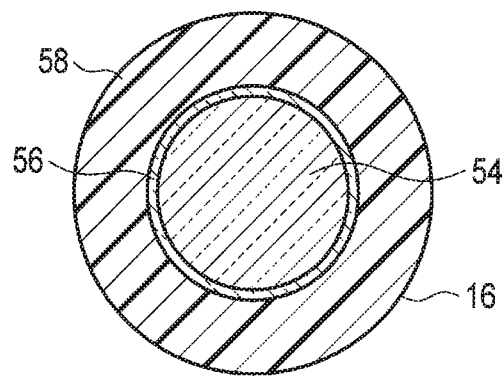
FIG. 2A is a cross-sectional view showing an example of the shape of a light guide.

An embodiment of the present invention will be described below with reference to the drawings.

As shown in FIG. 1, a curvature sensor 10 according to an embodiment of the present invention includes a light source 12, an optical branch 14, a light guide 16, a light reflector 18, a light detector 20, a light intensity monitor 22, a control and driving circuit 24, a calculation circuit 26 and an output device 30.

The light guide 16 is provided with a plurality of sensing parts, e.g. m sensing parts 32-1, 32-2, . . . , 32-$m$.

The calculation circuit 26 includes an input controller 34, a storage 36, a curvature calculator 38, a secondary information calculator 40 and an output controller 42. The storage 36 stores intensity modulation information 44, curvature characteristic information 46 and secondary information calculating information 48.

The configuration of each of the elements will be described in detail below.

The light source 12 includes, e.g. a semiconductor laser to generate sensor light. The optical branch 14 is composed of, e.g. a photocoupler to cause the sensor light generated by the light source 12 to be incident upon one end of the light guide 16. The light guide 16 guides the sensor light, which is incident upon the one end thereof by the optical branch 14, to the other end thereof, and emits the sensor light from the other end. The light reflector 18 reflects the light emitted from the other end of the light guide 16 and causes the light to be incident upon the other end of the light guide 16 again. Thus, the light guide 16 guides the light incident upon the other end thereof to the one end thereof and emits the light from the one end. The optical branch 14 supplies the light emitted from the one end of the light guide 16 to the light detector 20. The light detector 20 detects the intensities of light of predetermined wavelengths in the input light, and outputs information of the detected light intensities to the calculation circuit 26.

The light intensity monitor 22 detects the light intensities of the sensor light emitted from the light source 12 and supplies a result of the detection to the control and driving circuit 24 as light source light intensity information. The control and driving circuit 24 controls on/off operations of the light source 12 and the light detector 20. Furthermore, the control and driving circuit 24 controls the sensor light emitted from the light source 12 to have a desired light intensity based on the light source light intensity information from the light intensity monitor 22, and make a gain adjustment such that the output of the light detector 20 falls within a predetermined range.

The light guide 16 is disposed to extend along the longitudinal axis direction of a mounting section where curvature information is to be detected by the curvature sensor 10, for example, an insertion section of an endoscope, and has flexibility such that it can be bent after the bending state of the mounting section.

Specifically, the light guide 16 can be formed of an optical fiber. FIG. 2A shows a cross-section structure of the light guide 16 in the radial direction that is orthogonal to the longitudinal axis direction of the optical fiber. The optical fiber includes a core 54 that exists in the center thereof to guide light, a clad 56 provided around the core 54 to confine light to the core 54 stably, and a jacket 58 for protecting the core 54 and the clad 56 from a physical shock and a thermal shock.

Figure 2B:
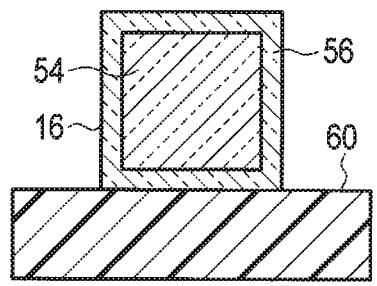
FIG. 2B is a cross-sectional view showing another example of the shape of a light guide.

Alternatively, the light guide 16 can be formed of an optical waveguide. As shown in FIG. 2B, the optical waveguide is formed by providing a core 54 and a clad 56 having a function equal to the function of those of the optical fiber, on a flexible substrate 60.

Figure 3A:
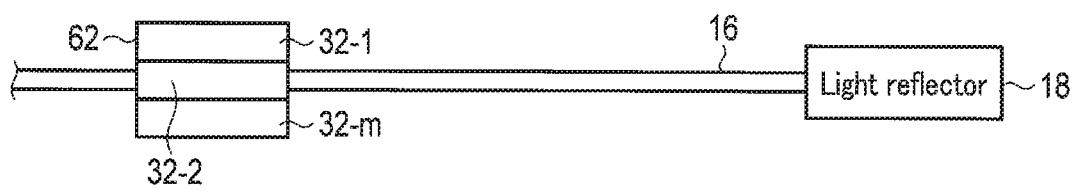
FIG. 3A is a schematic diagram illustrating a sensing part group.
Figure 3B:
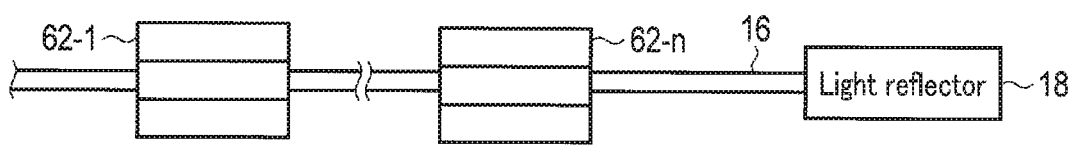
FIG. 3B is a schematic diagram illustrating a number of sensing part groups, which are provided in the longitudinal direction of the light guide.

Sensing parts are provided in each portion of the light guide 16, which corresponds to the position of the mounting section where curvature information is to be detected. The curvature information here is information on the direction of bending and the magnitude of bending. If the bending magnitude can be detected at least in two different directions, preferably in two orthogonal directions with respect to one portion where curvature information is to be detected, the bending direction of the portion can also be detected. It is thus necessary to form at least two sensing parts at each portion where curvature information is to be detected. Therefore, by using two light guides 16, a sensing part has only to be formed in each of the light guides 16 so as to correspond to one portion, and the light guides 16 have only to be incorporated into the mounting section such that the two sensing parts are oriented orthogonally. Alternatively, by using only one light guide 16, as shown in FIG. 3A, a plurality of sensing parts 32-1 to 32-$m$ have only to be formed, as a sensing part group 62, in different directions in the circumferential direction in substantially the same position in the longitudinal direction of the light guides 16. If, furthermore, there are many positions of the mounting section where the curvature is to be detected, the sensing part group 62 can be provided at each of the position. That is, as shown in FIG. 3B, n sensing part groups 62-1 to 62-$n$ may be formed at different positions in the longitudinal direction of the light guide 16. If a plurality of sensing parts are formed as the sensing part group 62, the number of light guides 16 can be reduced, and the diameter of the mounting section into which the light guides 16 are incorporated can be decreased.

Figure 4A:
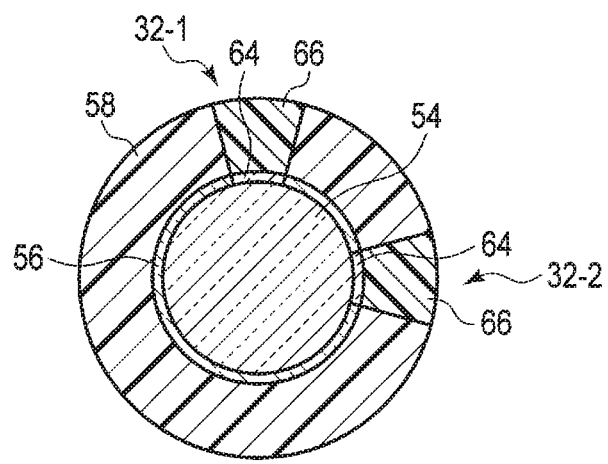
FIG. 4A is a cross-sectional view showing an example of a configuration of a sensing part in the light guide shown in FIG. 2A.
Figure 4B:
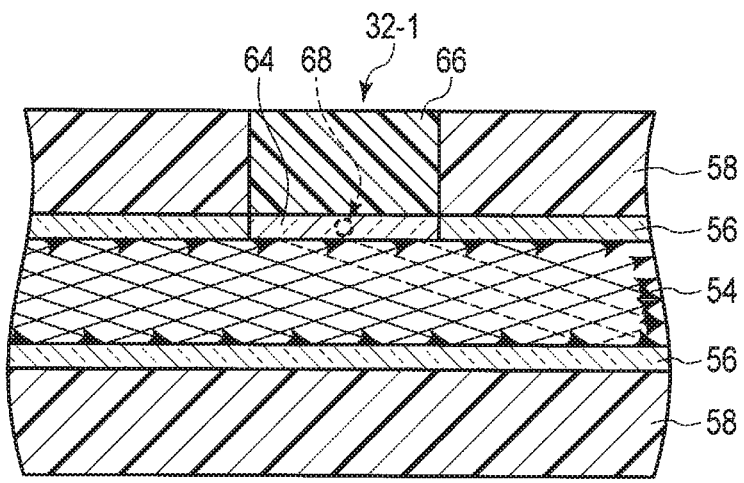
FIG. 4B is a cross-sectional view taken along the longitudinal direction of the sensing part in the light guide shown in FIG. 4A.

If at least two sensing parts are arranged for one sensing part group 62, the curvature information can be obtained. For example, as shown in FIG. 4A, two sensing parts 32-1 and 32-2 are formed in 90° different directions in the radial direction of the optical fiber that is the light guide 16. More specifically, as shown in FIGS. 4A and 4B, in the sensing parts 32-1 and 32-2, a sensing member 64 including an optical characteristic changing member is formed by removing the jacket 58 and the clad 56 at desired positions in the longitudinal axis direction of the optical fiber to expose part of the core 54. The optical characteristic changing member gives a change in optical characteristics different from those of the other sensing parts to light incident on the exposed part of the core 54 in accordance with the amount of bending in a specific direction. The sensing member 64 is made of a material having a flexibility or elasticity, such as a resin of acrylic type, epoxy type, silicon type or fluorine type, and soft water glass, and having a low refractive index, and formed to have a thickness approximately corresponding to that of the clad. A member like the jacket is filled, as a sensing part protecting member 66, in the part on the sensing part 64 from which the jacket 58 and the clad 56 have been removed, so that the original shape of the optical fiber is restored. It should be noted that the sensing part protector 66 may be substituted by the sensing member 64.

The jacket 58 and the clad 56 are removed by laser processing or by using a photo process, an etching process or the like. If a microscopic scratch is made on the core 54 when they are removed, the optical fiber may leak light or lose light to be guided, and may be weakened against bending. It is thus desirable to process the optical fiber by a method in which the core 54 is not damaged as much as possible.

Figure 5A:
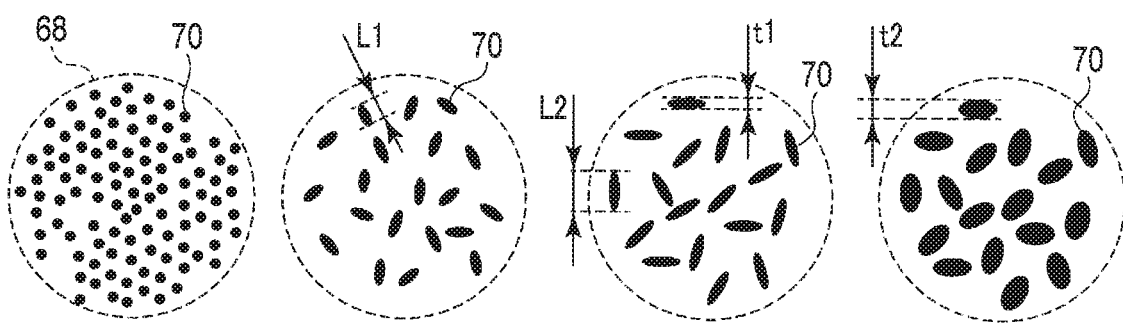
FIG. 5A is a diagram illustrating examples of the particle size of a plasmonic substance in a circular portion indicated by the broken line in FIG. 4B.

As shown in FIG. 5A which is enlarged views of a portion 68 of the sensing member 64, the sensing member 64 includes optical characteristic changing members 70 made of metal particles, which absorb light in a predetermined wavelength region. The optical characteristic changing members 70 have a special spectral absorption spectrum different from the spectral absorption spectrum peculiar to the metal. For example, the optical characteristic changing members 70 have a photoexcited plasmon generating function capable of exciting plasmons with light of at least one type of light source. The optical characteristic changing members 70 is metal nanoparticles having, as an absorption spectrum, a sum of a spectral absorption spectrum peculiar to a metal and a special absorption spectrum due to a surface plasmon effect. The photoexcited plasmon generating function is composed of one of at least one type of plasmonic substance, nanosized material, nanosized mineral, and nanosized metal. The plasmonic substance here is a substance having a state in which free electrons collectively oscillate and behave as pseudo particles. The "nanosized" means less than 1 μm. The metal particles are, for example, Au, Ag, Cu and Pt, and are dispersion media. The shape of the metal particle is a sphere or a cylinder or a polygonal prism.

Figure 5B:
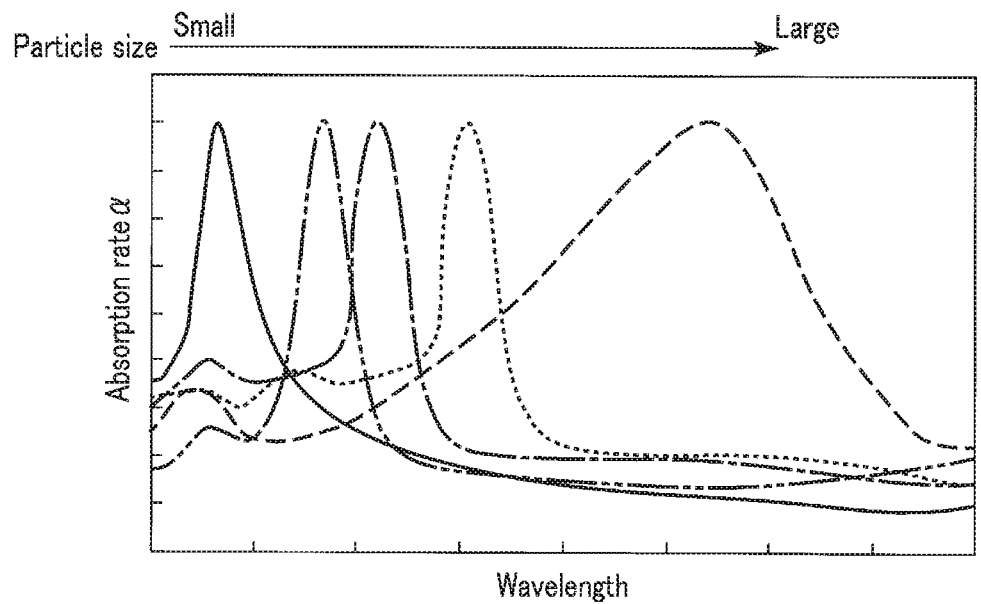
FIG. 5B is a diagram showing examples of a special spectroscopic absorption spectrum according to the particle size of the plasmonic substance.

The photoexcited plasmon generating function varies in special spectral absorption spectrum if the metal particles of, e.g. the optical characteristic changing member 70 differ in at least one of size, length and thickness as shown in FIG. 5A. For example, as shown in FIG. 5B, as the particle size increases, the peak wavelength (absorption wavelength characteristic region) of the light absorption rate moves toward the longer wavelength side. In the sensing parts, therefore, as the optical characteristic changing member 70, there is a combination having k special spectral absorption spectrums with the same metal element.

Figure 6:
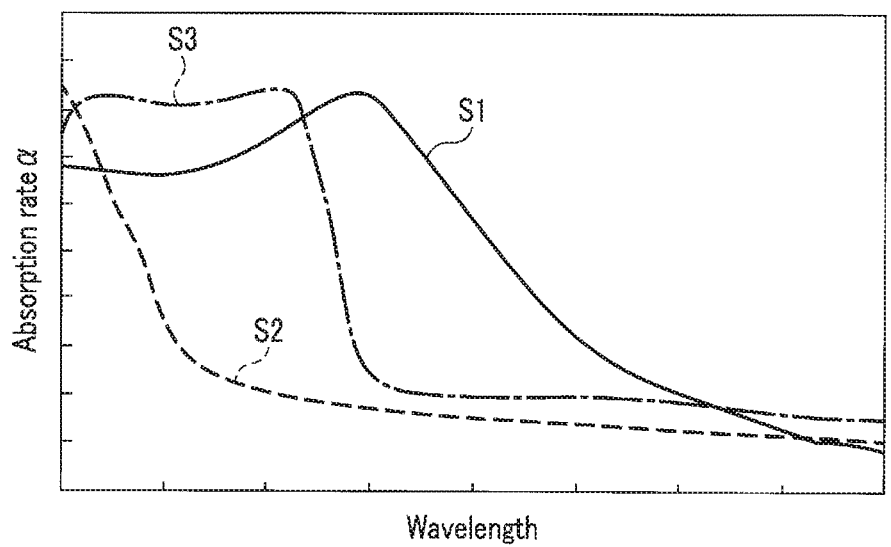
FIG. 6 is a diagram showing examples of special spectroscopic absorption spectrums of plasmonic substances used in each sensing part in the sensing part group.

Furthermore, if another optical characteristic changing member 70, e.g. another metal particle is used, the photoexcited plasmon generating function has a different special spectral absorption spectrum as shown in FIG. 6.

Furthermore, a composite optical characteristic changing member obtained by mixing a plurality of metal particles can be used.

Since a plurality of optical characteristic changing members 70, for example, a plurality of metal particles are caused to differ in at least one size, length and thickness, sensing members 64 having different special spectral absorption spectra can be achieved, and a large number of sensing parts that give an optical characteristic change different from that of other sensing parts can be formed.

Figure 7:
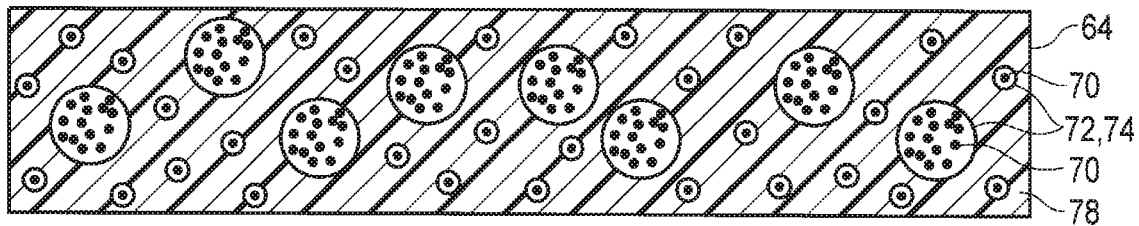
FIG. 7 is a schematic diagram showing an example of a plasmonic substance formed in a sensing part.

Incidentally, when the optical characteristic changing members 70 are to be mixed with a low refractive index resin or the like, which is a base material of the sensing member 64, aggregation occurs (the optical characteristic changing members 70 are not dispersed in the low refractive index resin, but separated and precipitated), and the light absorption characteristic peculiar to nanoization disappears or may not work sufficiently. As a method for preventing this, one or a plurality of optical characteristic changing members 70 may be surrounded by a dispersant 72 such as a surfactant or a capsule 74 as shown in FIG. 7. In addition, as the base material of the sensing member 64, for example, a low refractive index resin 78 with an aggregation inhibitor can be used to prevent aggregation between the optical characteristic changing members 70.

In the sensing parts 32-1 and 32-2 having the foregoing structure, when the optical fiber as the light guide 16 is bent, a very small part of the light transmitted through the optical fiber leaks into the sensing member 64. In other words, the sensing parts 32-1 and 32-2 are provided on one side of the optical fiber, and the amount of the leaked light (some light that leaks) varies according to the bending of the optical fiber. The sensing parts 32-1 and 32-2 vary the amount of optical characteristic change given to light according to the bending of the optical fiber. In other words, they vary the amount of light transmission of optical signals to which the optical characteristic change is given.

Figure 8A:
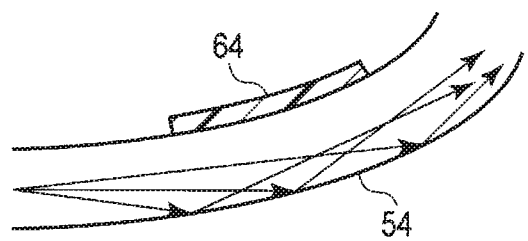
FIG. 8A is an illustration of the principle of the curvature sensor, in which the light guide is curved in the upward direction of this page.
Figure 8B:
FIG. 8B is an illustration of the principle of the curvature sensor, in which the light guide is not curved.
Figure 8C:
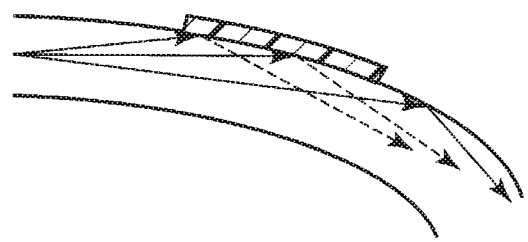
FIG. 8C is an illustration of the principle of the curvature sensor, in which the light guide is curved in the downward direction of this page.

FIGS. 8A, 8B and 8C are schematic views of light transmission amounts corresponding to the bending of the optical fiber. FIG. 8A shows the light transmission amount when the optical fiber is bent toward the side on which the sensing member 64 of the sensing parts 32-1 and 32-2 is provided. FIG. 8B shows the light transmission amount when the optical fiber is not bent, and FIG. 8C shows the light transmission amount when the optical fiber is bent toward the side opposite to the side on which the sensing member 64 is provided. As shown in FIGS. 8A, 8B and 8C, the light transmission amount is the largest when the optical fiber is bent toward the side on which the sensing member 64 is provided, followed by the light transmission amount when the optical fiber is not bent and then the light transmission amount when the optical fiber is bent to the side opposite to the side on which the sensing member 64 is provided. If, therefore, the light intensities of the optical signals emitted from the optical fiber are measured, the amounts of bending in the sensing parts 32-1 and 32-2 provided with the sensing member 64 can be detected. Since the positions in the radial direction of the optical fiber in which the sensing parts 32-1 and 32-2 are provided, namely, the directions of the sensing parts 32-1 and 32-2 are known, the bending direction can also be known, and the curvature information can be detected from the bending direction and the amounts of bending.

Figure 9:
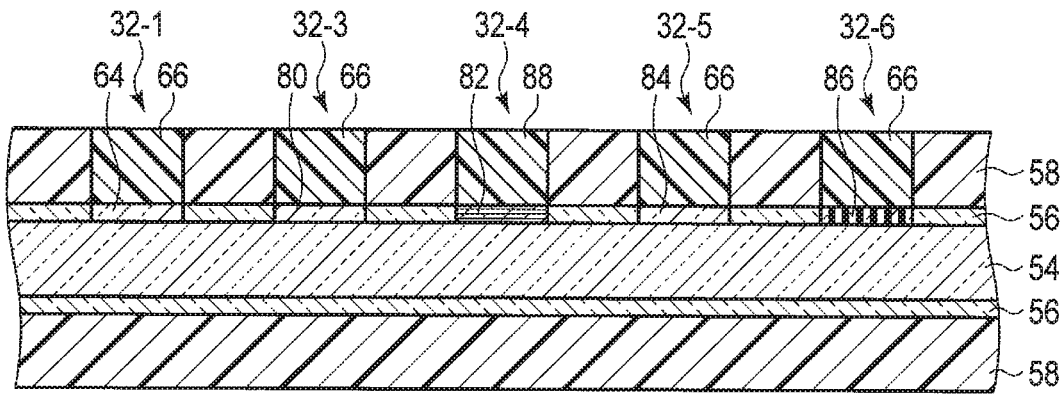
FIG. 9 is a sectional view taken along the longitudinal direction of the light guide, showing a number of sensing parts, which are arranged at different positions in the longitudinal direction of the light guide.

In the sensing parts, each sensing part can be formed of different optical characteristic changing members from other sensing parts. For example, as shown in FIG. 9, when five sensing parts 32-1, 32-3, 32-4, 32-5 and 32-6 are provided at different positions in the longitudinal direction of the optical fiber that is the light guide 16, they can have different optical characteristic changing members. The sensing member 64 of the sensing part 32-1 includes optical characteristic changing members 70 having a photoexcited plasmon generating function. A sensing member 80 of the sensing part 32-3 includes, for example, an optical characteristic changing member having a light absorption substance (also having a light scattering substance). A sensing member 82 of the sensing part 32-4 includes, for example, an optical characteristic changing member having a laminated dielectric film. A sensing member 84 of the sensing part 32-5 includes, for example, an optical characteristic changing member having a phosphor. A sensing member 86 of the detected part 32-6 includes, for example, an optical characteristic changing member having a grating structure. Of course, it is not indispensable to use all of these optical characteristic changing members for the sensing parts, but it is possible to use a combination of at least two of the optical characteristic changing members. The same applies to a plurality of sensing parts formed in different orientations at substantially the same position in the longitudinal direction of the optical fiber that is the light guide 16.

In the sensing member 80 of the sensing part 32-3, the sensing member 84 of the sensing part 32-5, and the sensing member 86 of the sensing part 32-6, a sensing part protector 66 is formed to restore the original shape of the optical fiber as in the sensing member 64 of the sensing part 32-1. In the sensing member 82 of the sensing part 32-4, a dielectric film effect increasing resin 88 is formed.

Figure 10:
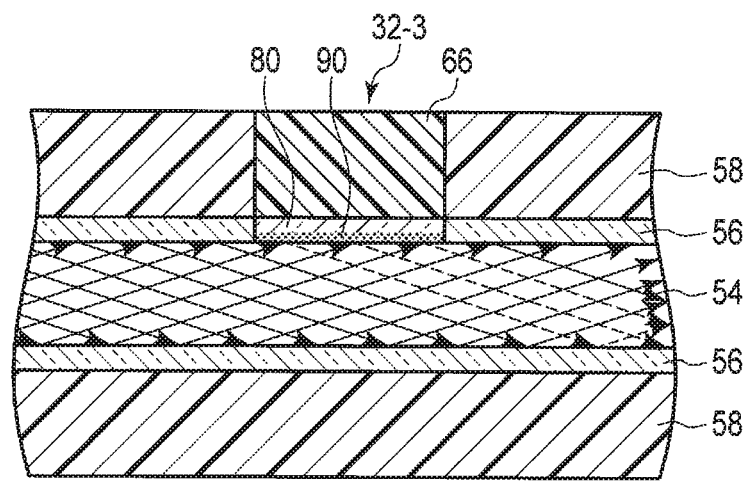
FIG. 10 is an illustration of evanescent light in a sensing part, using a coloring agent.

As shown in FIG. 10, the sensing part 32-3 has the same configuration as that of the sensing part 32-1 except that the sensing member 80 having a different optical characteristic changing member is used. The light absorbing substance of the optical characteristic changing member is a substance which causes absorption of different absorption amounts with respect to light of a wavelength overlapping at least part of at least one type of wavelength band in mutually different sensing parts. For example, the light absorbing substance contains nanosized pigment (mineral or chemically synthesized inorganic pigment or organic compound-based organic pigment) or dye (originally equal to or less than 1 nm).

As with the optical characteristic changing member 70 having the photoexcited plasmon generating function, the light absorbing substance can be surrounded by the dispersant 72 or the capsule 74, or the low refractive index resin 78 with an aggregation inhibitor or the like can be used as the base material of the sensing member 80.

Figure 11A:
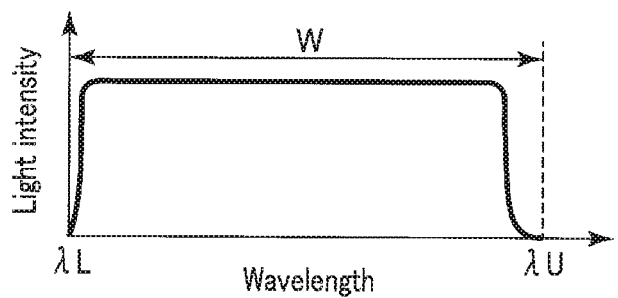
FIG. 11A is a diagram showing an example of a spectrum of light incident on the light guide.
Figure 11B:
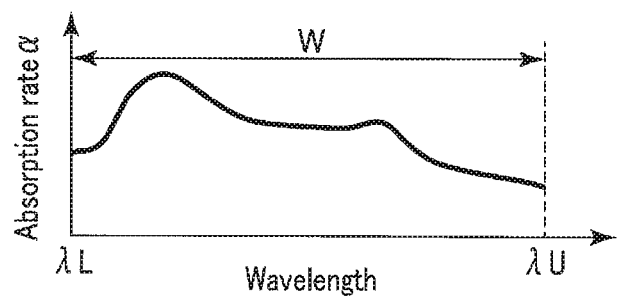
FIG. 11B is a diagram showing an example of an absorption spectrum of an absorption wavelength characteristic region generating member disposed in the sensing part.

The sensing member 80 of the sensing part 32-3 has an absorption spectrum as shown in FIG. 11B with respect to light from an ideal light source having a substantially uniform light spectrum in, for example, the wavelength band between $\lambda L$ and $\lambda U$ as shown in FIG. 11A, where W is the emission wavelength region of the ideal light source. When the light from the ideal light source strikes to the sensing member 80, the member 80 absorbs light contacting the core 54 and evanescent light 90 that has leaked into the clad 56 at the ratio of the absorption spectrum, and returns the remaining light to the core 54. This is shown in FIG. 10 as an easy-to-understand image. The solid line indicates light supplied from the light source 12. The light striking the sensing part 32-3 is absorbed by the absorption spectrum peculiar to the sensing part, and the remaining light is returned to the core 54 as indicated by the dotted arrow.

Figure 11C:
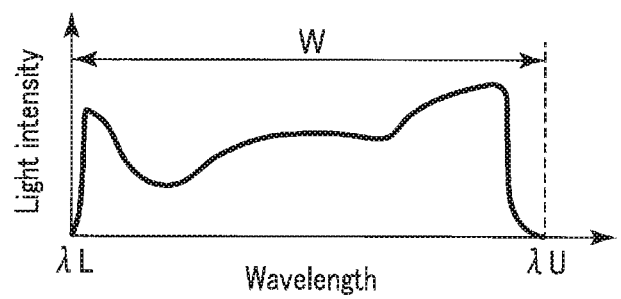
FIG. 11C is a diagram showing an example of a spectrum of light emitted from the light guide.

As the advantage of the sensing part 32-3, it is possible to lose the light supplied at an angle which is not less than the critical angle due to the optical fiber bent by the difference in refractive index between the core and the clad, and it is also possible to perform control by adjusting the refractive index of the clad 56 to be n1 or less with respect to n1 of the refractive index of the core 54. The substantially uniform light supplied from the light source is a spectrum optically influenced by the absorption spectrum of the sensing part 32-3 like the spectrum as shown in FIG. 11C.

Figure 12A:
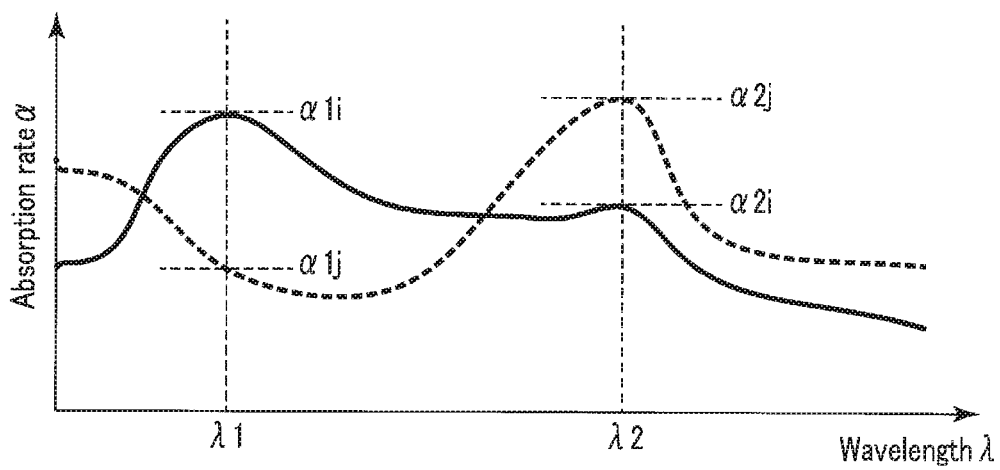
FIG. 12A is a diagram illustrating absorption wavelength characteristic regions of a plurality of absorption wavelength characteristic region generating members arranged in a sensing part.
Figure 12B:
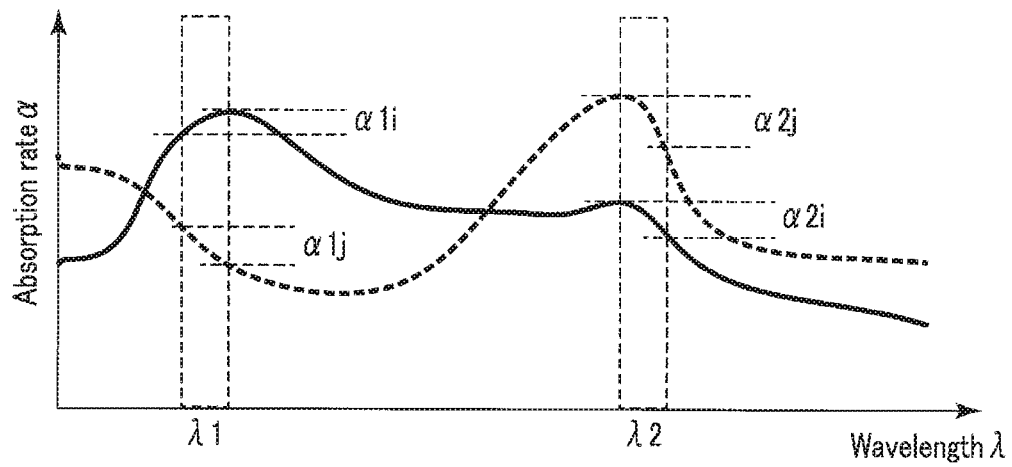
FIG. 12B is a diagram illustrating another example of the absorption wavelength characteristic regions.

The absorption wavelength characteristic region of the optical characteristic changing member included in the sensing member 80 of the sensing part 32-3 is set to differ from the absorption wavelength characteristic region of the optical characteristic changing member 70 included in the sensing member 64 of the sensing part 32-1. For example, FIG. 12A is a diagram showing the absorption spectra of light of the sensing members 64 and 80 set in the two sensing parts 32-1 and 32-3, in which the solid line indicates the sensing member 64 and the broken line indicates the sensing member 80. For example, when ideal light having a spectrum as shown in FIG. 11A is incident, the light intensities are attenuated at the spectrum ratios indicated by the solid line and the dotted line shown in FIG. 12A in the sensing members 64 and 80 of the sensing parts 32-1 and 32-3. The absorption wavelength characteristic region indicates, for example, regions of λ1 and λ2 in FIG. 12A. In the regions of λ1 and λ2, the absorptances α of different sensing parts 32-1 and 32-3 are different from each other. In the spectrum of the sensing part 32-1, the absorptance is α1$i$ at λ1 and the absorptance is α2$i$ at λ2. In the spectrum of the sensing part 32-3, the absorptance is α1$j$ at λ1 and the absorptance is α2$j$ at λ2. The absorptances α1$i$ and α1$j$ and the absorptances α2$i$ and α2$j$ are characterized in that they are different and the ratios between them are different at wavelengths λ1 and λ2. As described above, the absorption wavelength characteristic region indicates that there are a region such as λ1 and λ2 in which the sensing parts 32-1 and 32-3 are characterized by the ratios of absorption rates of a plurality of wavelengths in a wavelength band to be used. The wavelengths λ1 and λ2 may be a specific wavelength or may have a width in the wavelength band as shown in FIG. 12B.

The sensing parts 32-1 and 32-3 are separated by setting up the mathematical expression in which the sensing parts 32-1 and 32-3 maintain the intensity ratio of the absorption wavelength characteristic region and a difference between the light intensity of the light source 12 and the light intensity detected by the light detector 20 is the sum of changes in curvature, and by solving the mathematical expression. This expression will be described later.

Comparing the above configuration that applies a unique absorption wavelength characteristic region to each of the sensing parts with a configuration that causes no mutual absorption in the sensing parts, the way to apply the materials and absorption spectrum has a degree of freedom. Therefore, the former configuration makes it possible to provide a number of sensing parts for one light guide 16.

If a number of sensing parts can be provided for one light guide 16, when the light guide 16 is set in a narrow space, a plurality of items of curvature information of where the light guide 16 is placed, can be detected more accurately, in addition to the placement advantage. If it is applied to shape detection or the like using the curvature information, a more accurate shape can be detected.

Since, furthermore, a number of sensing parts can be detected by one light guide 16, the number of light supply sections can be reduced and so can be the number of detectors, which brings about the advantages of low costs and small size of the placement.

Figure 13:
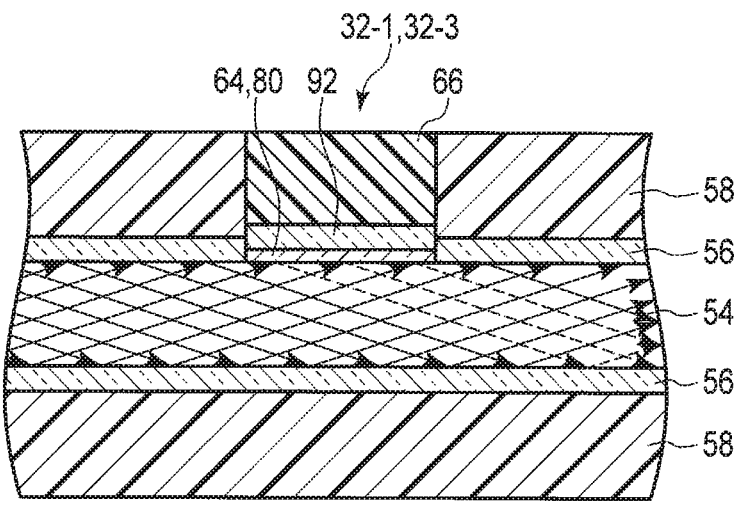
FIG. 13 is a cross-sectional view of the light guide, showing another configuration example of a sensing part using a coloring agent.

The sensing parts 32-1 and 32-3 have a refractive index that is larger than that of the light guide 16, specifically, the core 54. As shown in FIG. 13, in order to reflect the light incident on the sensing parts 32-1 and 32-3 from the light guide 16, the sensing parts 32-1 and 32-3 may further include a sensing part light confinement member 92 with a refractive index that is smaller than that of the core 54 of the light guide 16.

Figure 14:
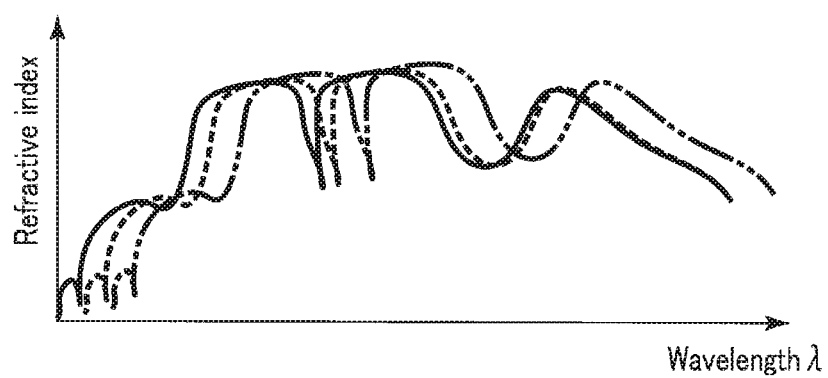
FIG. 14 is a diagram showing an example of reflection spectrum characteristics of a dielectric film.

Furthermore, the optical characteristic changing member of the sensing member 82 of the sensing part 32-4 has a laminated dielectric film. The dielectric has, for example, a reflection spectrum as shown in FIG. 14, and has a characteristic of absorbing light not reflected. In FIG. 14, the solid line indicates a case where light is incident on the laminated dielectric film at a certain incident angle a, the broken line indicates a case where light is incident at an incident angle b different from the above incident angle a, and the two-dot-one-dash line indicates a case where light is incident at an incidence angle c different from the incident angles a and b. Since the spectrum of the laminated dielectric film varies with the incidence angle of light, that is, the bending of the optical fiber, the information in the wavelength direction also varies. Although only one example is described here, it is possible to vary the spectrum by a lamination method of films having different refractive indices and thicknesses.

Though a sensing part having many absorption wavelength characteristic regions can be provided only by the foregoing photoexcited plasmon generating function and light absorbing substance, a sensing part having a larger number of absorption wavelength characteristic regions including the dielectric film can be provided.

By making the sensing member of a flexible resin material whose refractive index is adjusted like the clad material, a curvature sensor can be provided while maintaining the flexibility of the light guide 16. By changing the refractive index of a sensing member, the amount of leakage light can be controlled with respect to the bending amount of a sensing part, and the spectrum of the absorption wavelength characteristic region in the sensing part can be adjusted to easily make a difference from another sensing part. In other words, it is advantageous to increase the number of sensing parts.

Figure 15A:
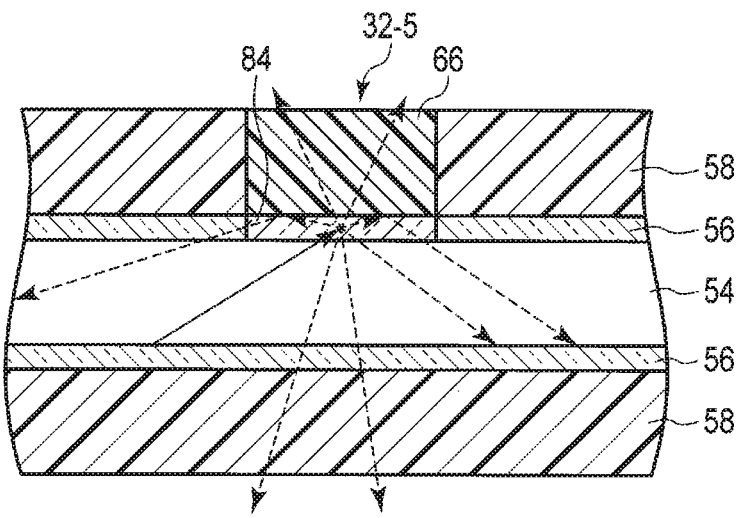
FIG. 15A is a cross-sectional view of the light guide, showing a configuration example of a sensing part using a fluorescent member.
Figure 15B:
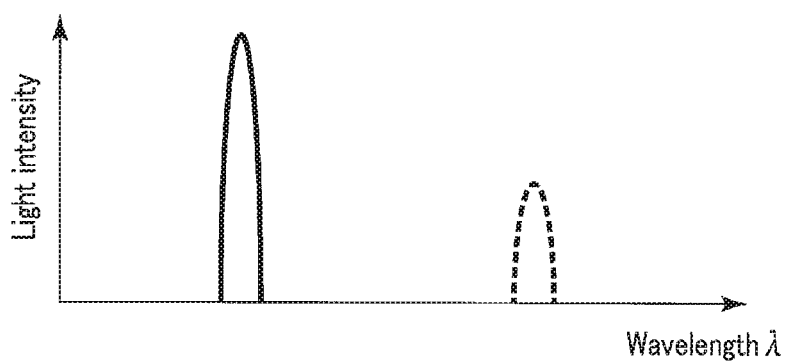
FIG. 15B is a diagram showing absorption characteristics and light emission characteristics of the fluorescent member.

Furthermore, the optical characteristic changing member of the sensing member 84 of the sensing part 32-5 has a phosphor. As shown in FIG. 15A, the sensing part 32-5 has the same configuration as that of the sensing part 32-1 except that a different optical characteristic changing member is used in the sensing member 84. The phosphor absorbs light on the short wavelength side as indicated by the solid line and has characteristics of generating light emission on the long wavelength side as indicated by the broken line, as shown in FIG. 15B. In this phosphor, the light conversion method differs from that of the sensing member 80, and the light striking the sensing part 32-5 is absorbed, and the sensing part 32-5 emits scattered light. In the present embodiment, the wavelength of this light emission is treated as an absorption wavelength characteristic region as described with respect to the photoexcited plasmon generating function and the light absorbing substance. The amount of light emission varies with the bending direction and the bending amount because the amount of light striking the phosphor increases and decreases with the bending amount. The use of the phosphor makes the detection sensitivity somewhat lower than the use of the sensing member 80.

Furthermore, the optical characteristic changing member of the sensing member 86 of the sensing part 32-6 has a grating structure. As shown in FIG. 16, the sensing part 32-6 has the same configuration as that of the sensing part 32-1 except that a different optical characteristic changing member is used in the sensing member 86. The sensing member 86 is formed so that a grating 94 is in contact with the core 54. The grating 94 may not be in contact with the core 54 or may be formed on part of the clad 56. The grating 94 causes a diffraction phenomenon when light propagates inside or reflects off the surface, and propagates light of a specific wavelength that goes in a predetermined direction different from the direction incident on the grating 94 so as to strengthen the light. In FIG. 16, the solid arrow indicates the light supplied from the light source 12 and the broken arrow indicates the light of a specific wavelength advanced in a predetermined direction by the grating 94. In the present embodiment, the specific wavelength of the light advanced by the grating 94 is treated as an absorption wavelength characteristic region as described with respect to the photoexcited plasmon generating function and the light absorbing substance.

The light source 12 will be described below. The light source 12 may employ a laser diode (LD), an LED and a lamp, or light obtained by causing a fluorescent agent to emit light by the light of these devices. These devices are combined to adjust light having a wavelength characteristic necessary for the curvature sensor 10 (e.g. white light) and emit the adjusted light. If the optical branch 14 is a fiber coupler, the light source here includes a lens system that collects light to be incident on the fiber of the fiber coupler, and the like. If the optical branch 14 is a half mirror or a beam splitter, the light source includes a lens system that adjusts the light to parallel light, and the like. Moreover, if return light influences the output as in the laser diode, the light source includes an isolator and the like.

Figure 17C:
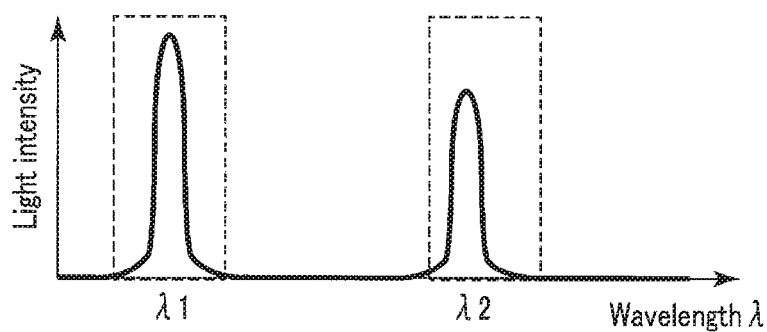
FIG. 17C is a diagram showing a relationship between the spectrum of light from the light source of FIG. 17A and another example of absorption wavelength characteristic regions.
Figure 17D:
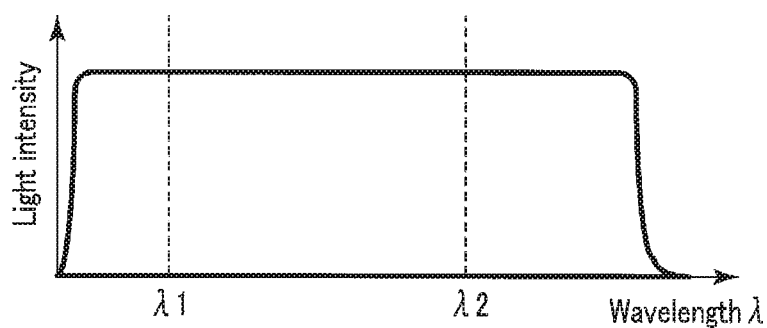
FIG. 17D is a diagram showing a relationship between a spectrum of light from an ideal light source and absorption wavelength characteristic regions.

The light source 12 needs to include at least part of the absorption wavelength characteristic region. Specifically, when the number of sensing parts is, e.g. two, the light source 12 can emit light generated by combining relatively narrow band light beams so as to include the absorption wavelength characteristic regions $\lambda 1$ and $\lambda 2$, as shown in FIG. 17A. Examples of the light source 12 in this case include an LED and an LD. Alternatively, as shown in FIG. 17B, the light source may emit light generated by exciting a phosphor with light of a low wavelength. With light having such a spectrum, the light source can easily include a plurality of absorption wavelength characteristic regions. In addition, when the absorption wavelength characteristic regions $\lambda 1$ and $\lambda 2$ each have a wavelength bandwidth as shown in FIG. 12B, the light source 12 has only to include part of a plurality of absorption wavelength characteristic regions, as shown in FIG. 17C. A light source that emits light having substantially uniform spectral characteristics in a plurality of absorption wavelength characteristic regions, as light which is easy to detect, is desirable as shown in FIG. 17D. This light source is preferable because the possibility of variations in detection accuracy is reduced.

Figure 18A:
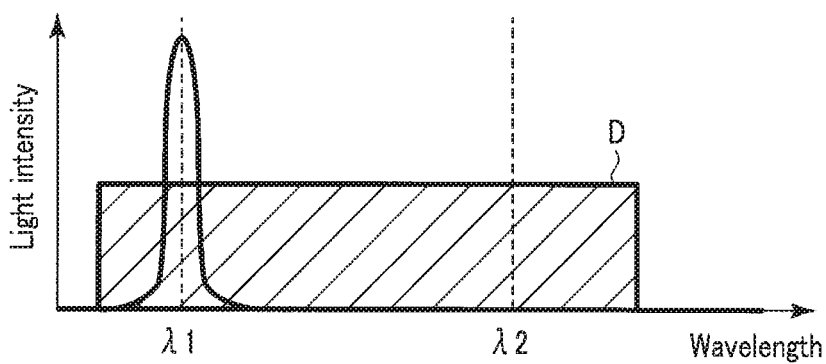
FIG. 18A is a diagram explaining a detection band of a light detector with respect to the spectrum of the light source.
Figure 18B:
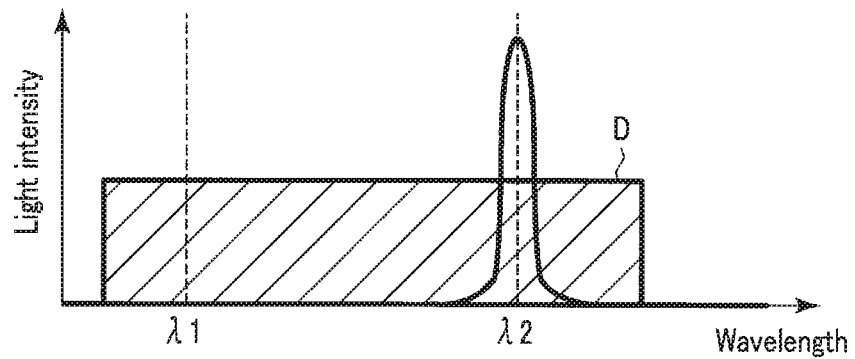
FIG. 18B is a diagram explaining the detection band of the light detector with respect to the spectrum of another light source.

Furthermore, the light source 12 does not emit light generated by synthesizing light of a relatively narrow band as shown in FIG. 17A, but may emit a plurality of light sources having discrete wavelengths of light one by one and supply them to the optical fiber that is the light guide 16 as shown in FIGS. 18A and 18B. In this way, the light detector 20 has only to have a detection band D capable of detecting light of wavelengths of all absorption wavelength characteristic regions, and need not to use a device for separating and detecting the light intensity of each wavelength, such as a spectroscope. This configuration makes it possible to decrease the costs of the light detector 20 greatly.

Figure 19A:
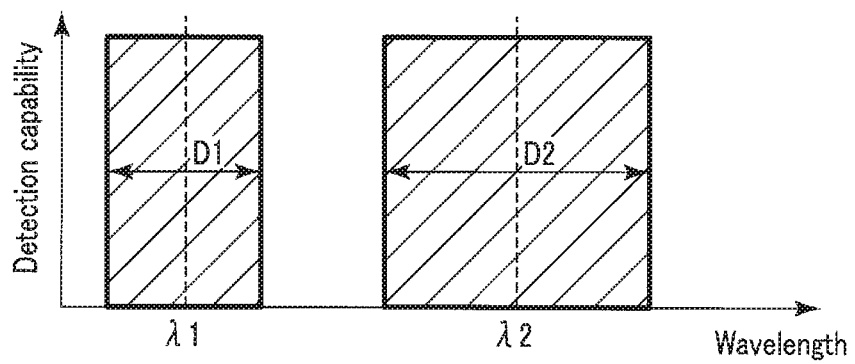
FIG. 19A is a diagram showing an example of the wavelength band of the light detector when the number of sensing parts is two.
Figure 19B:
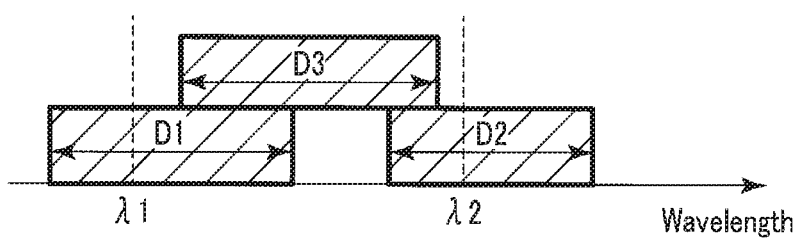
FIG. 19B is a diagram showing an example of the wavelength band of the light detector when the number of sensing parts is three.

Of course, as the light detector 20, any device can be used if it can detect the characteristics of the absorption wavelength characteristic regions applied to the sensing parts. Describing the configuration of the light detector 20 by the wavelength band, the characteristics are as follows. When the number of sensing parts is two, two bands D1 and D2 corresponding to the absorption wavelength characteristic regions or including the absorption wavelength characteristic regions can be detected, as shown in FIG. 19A. For the bands to be detected, the characteristics of the absorption wavelength characteristic regions have only to be retained. For example, when the number of sensing parts is three, it does not matter that bands D1, D2 and D3 of the light detector 20 are overlapped each other, as shown in FIG. 19B, depending on the wavelength region with the characteristics of the absorption wavelength characteristic regions.

As described above, the light detector 20 receives an optical signal of each absorption wavelength characteristic region whose transmission amount has been changed according to the bending state of each sensing part, detects the intensity of light of each absorption wavelength characteristic region, and outputs detected light intensity information. The detected light intensity information is information representing the relationship between each absorption wavelength characteristic region and the light intensity in the absorption wavelength characteristic region.

The input controller 34 of the calculation circuit 26 transmits the detected light intensity information to the curvature calculator 38 from the light detector 20. The control and driving circuit 24 supplies information of the intensity of light emitted from the light source 12, the gain of the light detector 20 and the like.

The storage 36 stores various types of information necessary for calculation to be performed by the curvature calculator 38. The storage 36 stores intensity modulation information 44, curvature characteristic information 46, secondary information calculating information 48 and the like in addition to a program including a calculation algorithm, for example.

The curvature calculator 38 can calculate curvature information of each sensing part based on the detected light intensity information acquired via the input controller 34 and the information stored in the storage 36. However, the larger the number of sensing parts, the longer the calculation time to calculate curvature information for each sensing part. In the present embodiment, therefore, curvature information of the sensing part groups 62-1 to 62-n is calculated based on the intensity modulation information 44 and the curvature characteristic information 46, which will be described later. In the present invention, the curvature information may be of course calculated for each sensing part.

The curvature calculator 38 includes a first calculator 50 and a second calculator 52. The first calculator 50 calculates light intensity change information for each sensing part based on the detected light amount information acquired via the input controller 34 and the intensity modulation information 44 stored in the storage 36. The second calculator 52 calculates curvature information in the sensing part groups 62-1 to 62-n based on the light intensity change information calculated by the first calculator 50 and the curvature characteristic information 46 stored in the storage 36. The curvature calculator 38 transmits the calculated curvature information to the secondary information calculator 40 and the output controller 42. The curvature calculator 38 may output information on the operation of the light detector 20 necessary for calculating the curvature information, such as the gain of the light detector 20, to the control and driving circuit 24 via the input controller 34.

The secondary information calculator 40 includes a CPU, an ASIC and the like. On the basis of the curvature information of the sensing part groups 62-1 to 62-n calculated by the curvature calculator 38, the secondary information calculator 40 calculates secondary information, such as the shape and state of the light guide 16 in which the sensing part groups 62-1 to 62-n are arranged, namely, a mounting portion for detecting curvature information by the curvature sensor 10, such as the insertion section of an endoscope. The calculated secondary information is transmitted to the output controller 42.

Note that the "state" in this embodiment includes not only a shape state such as a straight line and a U shape but also a state to determine a normal state or an abnormal state unique to the apparatus equipped with the curvature sensor 10. The abnormal state unique to the apparatus is, for example, a state in which the insertion section to be moved stops at the position and the curvature changes, which is called buckling in the field of the endoscope. The state varies depending on, e.g. the use, use condition and use environment of the apparatus. The "state" also includes a motion state such as extension of a subject, for example, when the subject has flexibility. The force by which the insertion section is advanced due to a movement of the subject is absorbed, and the insertion section to be advanced is only moved in parallel, which may cause what is called a skid in which the distal end of the insertion section does not move or the curvature of the insertion section does not change. The "state" also includes such a motion state of the subject. Furthermore, the secondary information may also include operation support information that supports, e.g. the insertion operation of the apparatus equipped with the curvature sensor 10.

The output controller 42 outputs the curvature information of the sensing part groups 62-1 to 62-n acquired from the curvature calculator 38 and the secondary information acquired from the secondary information calculator 40 to the output device 30.

The calculation that is performed by the curvature calculator 38 when the curvature sensor 10 is used will be described below.

First, for the sake of brevity, consider a case where a portion of the light guide 16 including one sensing part group 62 having two sensing parts 32-1 and 3-2 as shown in FIG. 4A has a length L and is curved at angle θ and curvature κ. In this case, the angle θ and the curvature κ, that is, the curvature information in the sensing part group 62 are obtained as follows.

First, in the first calculator 50, a simultaneous linear equation with two unknowns represented by the following equations (1) obtained according to the intensity modulation information 44 is solved for curvature characteristic information $\alpha(\theta, \kappa)$ and $\beta(\theta, \kappa)$ on the basis of the detected light intensity information $D_{\lambda 1}$ and $D_{\lambda 2}$ at the first and second wavelengths λ1 and λ2 that are the absorption wavelength characteristic regions of the sensing parts 32-1 and 32-2 detected by the light detector 20.

$$\begin{cases} \ln[D_{\lambda 1}(\theta, \kappa)] - \ln(I_{\lambda 1}) = \alpha(\theta, \kappa) \cdot U_{\alpha_{\lambda 1}} + \beta(\theta, \kappa) \cdot U_{\beta_{\lambda 1}} \\ \ln[D_{\lambda 2}(\theta, \kappa)] - \ln(I_{\lambda 2}) = \alpha(\theta, \kappa) \cdot U_{\alpha_{\lambda 2}} + \beta(\theta, \kappa) \cdot U_{\beta_{\lambda 2}} \end{cases} \quad (1)$$

In the above equation, $I_{\lambda 1}$ and $I_{\lambda 2}$ are reference light intensity information, which represents the light intensity of light of wavelength λn detected by the light detector 20 when the sensing part group 62 takes a predetermined shape as a reference (referred to as a reference curvature state hereinafter). Furthermore, $U_{\alpha \lambda 1}$, $U_{\beta \lambda 1}$, $U_{\alpha \lambda 2}$ and $U_{\beta \lambda 2}$ are intensity modulation information on the sensing parts 32-1 and 32-2 of the sensing part group 62. The reference light intensity information and intensity modulation information are acquired in advance and stored in the storage 36 as the intensity modulation information 44. The first calculator 50 can thus calculate light intensity change information α and β in the sensing parts 32-1 and 32-2 of the sensing part group 62, based on the detected light amount information $D_{\lambda 1}$ and $D_{\lambda 2}$ and the reference light amount information $I_{\lambda 1}$, $I_{\lambda 2}$ and the intensity modulation information $U_{\alpha \lambda 1}$, $U_{\beta \lambda 1}$, $U_{\alpha \lambda 2}$ and $U_{\beta \lambda 2}$.

Next, in the second calculator 52, a simultaneous equation with two unknowns represented by the following equation (2) obtained according to the light intensity change information α and β calculated by the first calculator 50 and $\alpha(\theta, \kappa)$ and $\beta(\theta, \kappa)$ which are the curvature characteristic information 46 stored in the storage 36, is solved for angle θ and curvature κ.

$$\begin{cases} \alpha(\theta, \kappa) = a_\alpha(\kappa) \cdot \sin[\theta + b_\alpha(\kappa)] + c_\alpha(\kappa) \\ \beta(\theta, \kappa) = a_\beta(\kappa) \cdot \sin[\theta + b_\beta(\kappa)] + c_\beta(\kappa) \end{cases} \quad (2)$$

It is thus possible to obtain the curvature information of the sensing part group 62, namely, the angle θ and the curvature κ in the sensing part group 62, in other words, the bending direction and the bending magnitude of the sensing part group 62. Note that the relationship in light intensity information is not limited to the one expressed in the form of the function as described above, but may be expressed by a table (look-up table) that stores the relationship between the wavelength and the light intensity.

The curvature information derivation calculation using the curvature characteristic information 46 has been described with the parameter representing the bending magnitude of the sensing part group being as a curvature. However, the curvature information derivation calculation using another parameter such as the radius of curvature and its corresponding curvature characteristic information can be adopted.

Consider two sensing part groups each having two sensing parts. More specifically, consider that in the light guide 16, a first portion having the length $L_1$ including a first sensing part group is curved at angle $\theta_1$ and curvature $\kappa_1$ and a second portion which is contiguous to the first portion and has the length $L_2$ including a second sensing part group is curved at angle $\theta_2$ and curvature $\kappa_2$.

In this case, angles $\theta_1$ and $\theta_2$ and curvatures $\kappa_1$ and $\kappa_2$ in the first sensing part group and the second sensing part group are obtained as follows.

First, in the first calculator 50, a simultaneous linear equation with four unknowns represented by the following equation (3) is solved for $\alpha_1(\theta_1, \kappa_1)$, $\beta_1(\theta_1, \kappa_1)$, $\alpha_2(\theta_2, \kappa_2)$, and $\beta_2(\theta_2, \kappa_2)$ on the basis of the detected light intensity information $D_{\lambda 1}$, $D_{\lambda 2}$, $D_{\lambda 3}$ and $D_{\lambda 4}$ at the first, second, third and fourth wavelengths λ1, λ2, λ3 and λ4 detected by the light detector 20.

$$\begin{cases} \ln[D_{\lambda 1}(\theta_1, \kappa_1, \theta_2, \kappa_2)] - \ln(I_{\lambda 1}) = \alpha_1(\theta_1, \kappa_1) \cdot U_{\alpha_{1_{\lambda 1}}} + \beta_1(\theta_1, \kappa_1) \cdot \\ \quad U_{\beta_{1_{\lambda 1}}} + \alpha_2(\theta_2, \kappa_2) \cdot U_{\alpha_{2_{\lambda 1}}} + \beta_2(\theta_1, \kappa_1) \cdot U_{\beta_{2_{\lambda 1}}} \\ \ln[D_{\lambda 2}(\theta_1, \kappa_1, \theta_2, \kappa_2)] - \ln(I_{\lambda 2}) = \alpha_1(\theta_1, \kappa_1) \cdot U_{\alpha_{1_{\lambda 2}}} + \beta_1(\theta_1, \kappa_1) \cdot \\ \quad U_{\beta_{1_{\lambda 2}}} + \alpha_2(\theta_2, \kappa_2) \cdot U_{\alpha_{2_{\lambda 2}}} + \beta_2(\theta_1, \kappa_1) \cdot U_{\beta_{2_{\lambda 2}}} \\ \ln[D_{\lambda 3}(\theta_1, \kappa_1, \theta_2, \kappa_2)] - \ln(I_{\lambda 3}) = \alpha_1(\theta_1, \kappa_1) \cdot U_{\alpha_{1_{\lambda 3}}} + \beta_1(\theta_1, \kappa_1) \cdot \\ \quad U_{\beta_{1_{\lambda 3}}} + \alpha_2(\theta_2, \kappa_2) \cdot U_{\alpha_{2_{\lambda 3}}} + \beta_2(\theta_1, \kappa_1) \cdot U_{\beta_{2_{\lambda 3}}} \\ \ln[D_{\lambda 4}(\theta_1, \kappa_1, \theta_2, \kappa_2)] - \ln(I_{\lambda 4}) = \alpha_1(\theta_1, \kappa_1) \cdot U_{\alpha_{1_{\lambda 4}}} + \beta_1(\theta_1, \kappa_1) \cdot \\ \quad U_{\beta_{1_{\lambda 4}}} + \alpha_2(\theta_2, \kappa_2) \cdot U_{\alpha_{2_{\lambda 4}}} + \beta_2(\theta_1, \kappa_1) \cdot U_{\beta_{2_{\lambda 4}}} \end{cases} \quad (3)$$

The reference light intensity information $I_{\lambda 1}$, $I_{\lambda 2}$, $I_{\lambda 3}$ and $I_{\lambda 4}$ and the intensity modulation information $U\alpha_{1 \lambda 1}$, $U\alpha_{1 \lambda 2}$, $U\beta_{1 \lambda 3}$, $U\alpha_{1 \lambda 4}$, $U\beta_{1 \lambda 1}$, $U\beta_{1 \lambda 2}$, $U\beta_{1 \lambda 3}$, $U\beta_{1 \lambda 4}$, $U\alpha_{2 \lambda 1}$, $U\alpha_{2 \lambda 2}$, $U\alpha_{2 \lambda 3}$, $U\alpha_{2 \lambda 4}$, $U\beta_{2 \lambda 1}$, $U\beta_{2 \lambda 2}$, $U\beta_{2 \lambda 3}$ and $U\beta_{2 \lambda 4}$ are acquired in advance and stored in the storage 36 as the intensity modulation information 44. Therefore, in the first calculator 50, the light intensity change information $\alpha_1$, $\beta_1$, $\alpha_2$ and $\beta_2$ in the two sensing parts of the first sensing part group and the two sensing parts of the second sensing part group can be calculated.

Next, in the second calculator 52, a simultaneous equation with two unknowns represented by the following equation (4) obtained according to the light intensity change information $\alpha_1$ and $\beta_1$ calculated by the first calculator 50 and $\alpha_1(\theta_1, \kappa_1)$ and $\beta_1(\theta_1, \kappa_1)$ which are the curvature characteristic information 46 stored in the storage 36, is solved for angle $\theta_1$ and curvature $\kappa_1$.

$$\begin{cases} \alpha_1(\theta_1, \kappa_1) = a_{\alpha_1}(\kappa_1) \cdot \sin[\theta_1 + b_{\alpha_1}(\kappa_1)] + c_{\alpha_1}(\kappa_1) \\ \beta_1(\theta_1, \kappa_1) = a_{\beta_1}(\kappa_1) \cdot \sin[\theta_1 + b_{\beta_1}(\kappa_1)] + c_{\beta_1}(\kappa_1) \end{cases} \quad (4)$$

Furthermore, in the second calculator 52, a simultaneous equation with two unknowns represented by the following equation (5) obtained according to the light intensity change information $\alpha_2$ and $\beta_2$ calculated by the second calculator 52 and $\alpha_2(\theta_2, \kappa_2)$ and $\beta_2(\theta_2, \kappa_2)$ which are the curvature characteristic information 46 stored in the storage 36, is solved for angle $\theta_2$ and curvature $\kappa_2$.

$$\begin{cases} \alpha_2(\theta_2, \kappa_2) = a_{\alpha_2}(\kappa_2) \cdot \sin[\theta_2 + b_{\alpha_2}(\kappa_2)] + c_{\alpha_2}(\kappa_2) \\ \beta_2(\theta_2, \kappa_2) = a_{\beta_2}(\kappa_2) \cdot \sin[\theta_2 + b_{\beta_2}(\kappa_2)] + c_{\beta_2}(\kappa_2) \end{cases} \quad (5)$$

It is thus possible to obtain angle $\theta_1$ and curvature $\kappa_1$, namely, the curvature information in the first sensing part group and angle $\theta_2$ and curvature $\kappa_2$, namely, the curvature information in the second sensing part group.

This description is about a configuration in which two sensing part groups are provided in the light guide 16 at different positions in the longitudinal direction of the light guide 16; however, in a configuration in which more sensing part groups 62 are provided in the light guide 16, too, the curvature information of each of the sensing part groups 62 can be obtained by the same method. Specifically, the curvature information can be obtained as follows. Assume hire that the number of sensing part groups 62 is m, where the natural number from 1 to m is n (n=1, 2, ..., m).

$\alpha_n(\theta_n, \kappa_n)$ and $\beta_n(\theta_n, \kappa_n)$, which are the curvature characteristic information 46 of the (2n-1)-th sensing part and (2n)-th sensing part of the n-th sensing part group, are acquired by setting the sensing part groups other than the n-th sensing part group in the reference curvature state and varying angle $\theta_n$ and curvature $\kappa_n$ of the n-th sensing part group within a range in which they can be taken.

The curvature information is calculated as follows.

First, a simultaneous linear equation with 2m unknowns expressed by the following equation (6) is solved for $\alpha_n(\theta_n, \kappa_n)$ and $\beta_n(\theta_n, \kappa_n)$.

$$\begin{cases} \ln[D_{\lambda 1}(\theta_1, \kappa_1, \ldots, \theta_m, \kappa_m)] - \ln(I_{\lambda 1}) = \alpha_1(\theta_1, \kappa_1) \cdot U_{\alpha_{1_{\lambda 1}}} + \\ \beta_1(\theta_1, \kappa_1) \cdot U_{\beta_{1_{\lambda 1}}} + \ldots + \alpha_m(\theta_m, \kappa_m) \cdot U_{\alpha_{m_{\lambda 1}}} + \beta_m(\theta_m, \kappa_m) \cdot U_{\beta_{m_{\lambda 1}}} \\ \ln[D_{\lambda 2}(\theta_1, \kappa_1, \ldots, \theta_m, \kappa_m)] - \ln(I_{\lambda 2}) = \alpha_1(\theta_1, \kappa_1) \cdot U_{\alpha_{1_{\lambda 2}}} + \\ \beta_1(\theta_1, \kappa_1) \cdot U_{\beta_{1_{\lambda 2}}} + \ldots + \alpha_m(\theta_m, \kappa_m) \cdot U_{\alpha_{m_{\lambda 2}}} + \beta_m(\theta_m, \kappa_m) \cdot U_{\beta_{m_{\lambda 2}}} \\ \vdots \\ \ln[D_{\lambda 2m}(\theta_1, \kappa_1, \ldots, \theta_m, \kappa_m)] - \ln(I_{\lambda 2m}) = \alpha_1(\theta_1, \kappa_1) \cdot U_{\alpha_{1_{\lambda 2m}}} + \\ \beta_1(\theta_1, \kappa_1) \cdot U_{\beta_{1_{\lambda 2m}}} + \ldots + \alpha_m(\theta_m, \kappa_m) \cdot U_{\alpha_{m_{\lambda 2m}}} + \beta_m(\theta_m, \kappa_m) \cdot U_{\beta_{m_{\lambda 2m}}} \end{cases} \quad (6)$$

Next, a simultaneous equation with m-sets unknowns represented by the following equation (7) are solved for angle $\theta_n$ and curvature $\kappa_n$.

$$\begin{cases} \alpha_1(\theta_1, \kappa_1) = a_{\alpha_1}(\kappa_1) \cdot \sin[\theta_1 + b_{\alpha_1}(\kappa_1)] + c_{\alpha_1}(\kappa_1) \\ \beta_1(\theta_1, \kappa_1) = a_{\beta_1}(\kappa_1) \cdot \sin[\theta_1 + b_{\beta_1}(\kappa_1)] + c_{\beta_1}(\kappa_1) \end{cases} \quad (7)$$

$$\begin{cases} \alpha_2(\theta_2, \kappa_2) = a_{\alpha_2}(\kappa_2) \cdot \sin[\theta_2 + b_{\alpha_2}(\kappa_2)] + c_{\alpha_2}(\kappa_2) \\ \beta_2(\theta_2, \kappa_2) = a_{\beta_2}(\kappa_2) \cdot \sin[\theta_2 + b_{\beta_2}(\kappa_2)] + c_{\beta_2}(\kappa_2) \end{cases}$$

$$\vdots$$

$$\begin{cases} \alpha_m(\theta_m, \kappa_m) = a_{\alpha_m}(\kappa_m) \cdot \sin[\theta_m + b_{\alpha_m}(\kappa_m)] + c_{\alpha_m}(\kappa_m) \\ \beta_m(\theta_m, \kappa_m) = a_{\beta_m}(\kappa_m) \cdot \sin[\theta_m + b_{\beta_m}(\kappa_m)] + c_{\beta_m}(\kappa_m) \end{cases}$$

Thus, the curvature information $(\theta_n, \kappa_n)$ of each sensing part group 62 is obtained.

As described above, the curvature sensor 10 according to the present embodiment is a curvature sensor which detects curvature information from a plurality of optical signals derived from the sensing parts 32-1 to 32-m provided in the light guide 16 having flexibility, and includes the light source 12, the light guide 16, the sensing parts 32-1 to 32-m, and the light detector 20. The light source 12 generates sensor light in the emission wavelength regions including at least predetermined wavelength components. The light guide 16 is, for example, an optical fiber that has flexibility and confines and guides the sensor light. The sensing parts 32-1 to 32-m are formed in at least one of different positions in the longitudinal direction of the light guide 16 and different directions in a circumferential (bending) direction in substantially the same position in the longitudinal direction, and are made of a flexible member. Then, each sensing part gives an optical characteristic change, which differs from that of the other sensing parts, to the sensor light incident thereon in accordance with the amount of bending in a specific direction, thereby generating the optical signals having absorption wavelength characteristic regions that vary from sensing part to sensing part. The light detector 20 detects the optical signals included in the sensor light from the light source 12, which has passed through the sensing parts 32-1 to 32-m and undergone the optical characteristic change.

The curvature sensor 10 can detect the bending amount of each sensing part as an independent value by forming a plurality of sensing parts in a single light guide 16, which give an optical characteristic change different from that of the other sensing parts to the sensor light incident thereon in accordance with the amount of bending in a specific direction. It is therefore possible to detect the shape and state of a thin, tubular insert such as the insertion section of an endoscope (the detected state includes the force applied to the sensing parts in consideration of the rigidity of the tubular insert and a specific operating state (e.g. a state in which the tip is not advanced because of buckling, the tip is normally advanced, etc.)).

Furthermore, the curvature sensor 10 according to the present embodiment is a curvature sensor which detects curvature information from a plurality of optical signals derived from the sensing parts 32-1 to 32-m provided in the light guide 16 having flexibility, and includes the light source 12, the light guide 16, the sensing parts 32-1 to 32-m, and the light detector 20. The light source 12 generates sensor light in the emission wavelength regions including at least predetermined wavelength components. The light guide 16 is, for example, an optical fiber and a flexible waveguide, which confine and guide the sensor light. The sensing parts 32-1 to 32-m are formed in at least one of different positions in the longitudinal direction of the light guide 16 and different directions in a circumferential (bending) direction in substantially the same position in the longitudinal direction, and are made of an elastic material. Each sensing part is configured to include the optical characteristic changing member 70 which changes the optical characteristics of the sensor light guided by the light guide 16 in accordance with the amount of bending of the light guide 16 to generate the optical signals having absorption wavelength characteristic regions that vary from sensing part to sensing part. The light detector 20 detects the optical signals included in the sensor light from the light source 12, which has passed through the sensing parts 32-1 to 32-m and undergone the optical characteristic change. The optical characteristic changing member 70 is a member made of metal particles, which absorbs light in a predetermined wavelength range and has a special spectral absorption spectrum different from the spectral absorption spectrum peculiar to the metal. The optical characteristic changing members having different special spectral absorption spectra are arranged in the sensing parts 32-1 to 32-m, and the special spectral absorption spectra of all the optical characteristic changing members at least overlap the light emission wavelength region of the sensor light from the light source 12.

The curvature sensor 10 can detect the bending amount of each sensing part as an independent value by forming a plurality of sensing parts in a single light guide 16, the sensing parts having special spectral absorption spectra over a predetermined wavelength region, these special spectral absorption spectra differing from one another and at least overlapping with one another. It is therefore possible to detect the shape and state of a thin, tubular insert such as the insertion section of an endoscope (the detected state includes the force applied to the sensing parts in consideration of the rigidity of the tubular insert and a specific operating state (e.g. a state in which the tip is not advanced because of buckling, the tip is normally advanced, etc.)).

The curvature sensor 10 of the present embodiment further includes the curvature calculator 38 that calculates the curvature information from the optical signals detected by the light detector 20.

It is thus possible to calculate the curvature information from the combined wave of the optical signals with mutually different changes in the wavelength bands (spectra) overlapped with each other.

The curvature calculator 38 uses, as one sensing part group 62, the sensing parts formed in different directions in the circumferential direction in substantially the same position in the longitudinal direction of the light guide 16, to calculate the curvature information of the one sensing part group 62 from the optical signals detected by the detector 20.

It is thus possible to directly obtain the curvature information of the sensing parts at the positions where the sensing parts are arranged, without obtaining the curvature information of each of the sensing parts. Accordingly, the calculation time can be shortened.

Furthermore, in each of different positions in the longitudinal direction of the light guide 16 in which the sensing parts 32-1 to 32-m are formed, at least one sensing part is further formed in a different direction in the circumferential direction in substantially the same position to make a sensing part group in each of the different positions in the longitudinal direction. In other words, a plurality of sensing part groups 62-1 to 62-n are provided in the longitudinal direction. The curvature calculator 38 calculates the curvature information of each of the sensing part groups from the optical signals detected by the light detector 20.

It is thus possible to directly obtain the curvature information of the sensing parts at the positions where the sensing parts are arranged, without obtaining the curvature information of each of the sensing parts. Accordingly, the calculation time can be shortened. This advantage becomes conspicuous as the number of sensing parts increases.

The optical characteristic changing member has a photoexcited plasmon generating function capable of exciting plasmon with light of at least one type of light source.

Using such a material having a photoexcited plasmon generating function in the sensing parts, characteristic absorption can be performed in an optical range of a predetermined band.

The photoexcited plasmon generating function is composed of one of at least one type of plasmonic substance, nanosized material, nanosized mineral, and nanosized metal. The plasmonic substance is a substance having a state in which free electrons collectively oscillate and behave as pseudo particles. Insulators, metals, semiconductors, semimetals, large atoms, large molecules, etc. are known as substances in which plasmon is observed.

Since the sensing parts have the above substances, characteristic absorption can be performed in an optical range of a predetermined band.

In addition, the photoexcited plasmon generating function can be composed of one of at least one type of plasmonic substance, nanosized material, nanosized minerals, and nanosized metal, which differ in at least one of the size, length and thickness of the sensing parts 32-1 to 32-m.

Including these substances, the sensing parts can perform different characteristic spectrum absorptions in a light region of a predetermined band even though they are substances having the same plasmon generating function (same metal). It is therefore possible to increase the number of sensing parts easily without increasing the number of substances.

The optical characteristic changing member may be configured to include a light absorbing material (also including a light scattering material) which absorbs light having at least overlapping wavelengths of at least one type of wavelength band by different absorption amounts in mutually different sensing parts.

Using such a light absorbing material, the sensing parts can perform characteristic absorption in a light region of a predetermined band.

The light absorbing material is a dye or a pigment whose particles are nanosized (a mineral or a chemically synthesized inorganic pigment, or an organic pigment containing an organic compound as a component).

Even substances that largely inhibit the progress of light, such as a pigment can perform characteristic absorption in the light region of a predetermined band by miniaturizing the substances and reducing the density thereof. It is therefore possible to easily increase the number of sensing parts in the curvature sensor.

It is preferable that the optical characteristic changing member be configured to surround the photoexcited plasmon generating function or the light absorbing material with the dispersant 72 or the capsule 74.

More specifically, by surrounding the photoexcited plasmon generating function or the light absorbing material with the dispersant 72 or the capsule 74, the characteristics are stabilized, and aggregation is difficult to cause when they are mixed in the base material of the sensing parts. When the optical characteristic changing member is to be mixed with a low refractive index resin or the like, which is the base material of the sensing parts, aggregation is caused (the optical characteristic changing member is not dispersed in the low refractive index resin but separated and precipitated). Thus, the light absorption characteristic may be lost or may not work sufficiently. As a method for preventing this, it is effective to surround the photoexcited plasmon generating function or the light absorbing material with a specific dispersant 72 or the capsule 74.

Furthermore, for example, a low refractive index resin to which an aggregation inhibitor is added may be used as the base material of the sensing parts.

Furthermore, the sensing parts 32-1 to 32-*m* can be composed of different optical characteristic changing members. In this case, the optical characteristic changing members are the combination of at least two types of the photoexcited plasmon generating function, the light absorbing material, and the grating structure provided in the sensing parts so as to be in contact with the light guide.

By combining a plurality of optical characteristic changing members having different principles, the number of sensing parts can be increased much more easily.

Furthermore, the sensing parts 32-1 to 32-*m* have a refractive index that is larger than that of the light guide 16, and can be configured to include the sensing part light confinement member 92 having a refractive index that is smaller than that of the light guide 16 to reflect light incident upon the sensing parts 32-1 to 32-*m* from the light guide 16.

There is not much choice of low refractive index resin as an option from the viewpoint of the whole resin. Therefore, even though the optical characteristic changing member is difficult to configure (difficult to mix, difficult to dye), if this configuration is employed, resin can be selected regardless of the refractive index, and the number of sensing parts can be increased.

Furthermore, the light detector 20 has detection wavelength bands the number of which is equal to or larger than the number of sensing parts 32-1 to 32-*m*.

If the number of sensing parts is increased, it is necessary to increase the number of detection wavelength separation elements of the light detector. The most expensive way is to use a spectrometer. To make it cheap is to mount a color filter or a filter using light interference on a photoelectric conversion element (including on-chip). In this case, if overlapping of the bands to be detected can be permitted, the light detector 20 can be provided more easily and inexpensively.

Furthermore, the light source 12 uses a device that emits sensor light in the emission wavelength region, including at least the wavelength component of the absorption wavelength characteristic regions or at least part of the wavelength component of the absorption wavelength characteristic regions.

More specifically, the light source 12 needs to include at least part of the absorption wavelength characteristic regions. For example, when there are two sensing parts, it synthesizes relatively narrow band light to include the absorption wavelength characteristic regions λ1 and λ2, as shown in FIG. 17A. If the light is as shown in FIG. 17B, the light source can easily include a plurality of absorption wavelength characteristic regions. That is, the light source 12 may include part of the absorption wavelength characteristic regions, as shown in FIG. 17C.

Moreover, the light source 12 emits the sensor light in the emission wavelength region having substantially uniform light intensity in all the wavelength components of the absorption wavelength characteristic regions.

If the light source is a light source having substantially uniform spectral characteristics in a plurality of absorption wavelength characteristic regions, as shown in FIG. 17D, it is more favorable because the possibility of occurrence of variations in detection accuracy decreases.

The sensing parts 32-1 to 32-*m* may further include at least one of a narrow-band absorption member having absorption characteristics only in a short range of the wavelength band and a fluorescent member which absorbs predetermined light and generates a spectrum of another wavelength. In this case, the light source 12 is capable of supplying light of a wavelength necessary for the narrow-band absorption member and/or the fluorescent member, and the light detector 20 can detect a change of light by the narrow-band absorption member and/or the fluorescent member.

This makes it possible to further increase the number of sensing parts formed in one light guide 16.

Furthermore, the light source 12 is composed of a plurality of discrete light sources. Each of the discrete light sources may emit light in a wavelength region which is part of a wavelength region within the emission wavelength region and which does not overlap the other discrete light sources, so as not to overlap temporally with the other discrete light sources.

In this case, the costs of the light detector 20 can be made very low.

Furthermore, the curvature sensor 10 according to the present embodiment can be mounted on an endoscope. In the present specification, the term "endoscope" is not limited to a medical endoscope or an industrial endoscope, but represents general devices including an insertion section to be inserted into an object to be inserted, such as forceps or a catheter.

A medical endoscope will be described below as an example of the endoscope.

Figure 20:
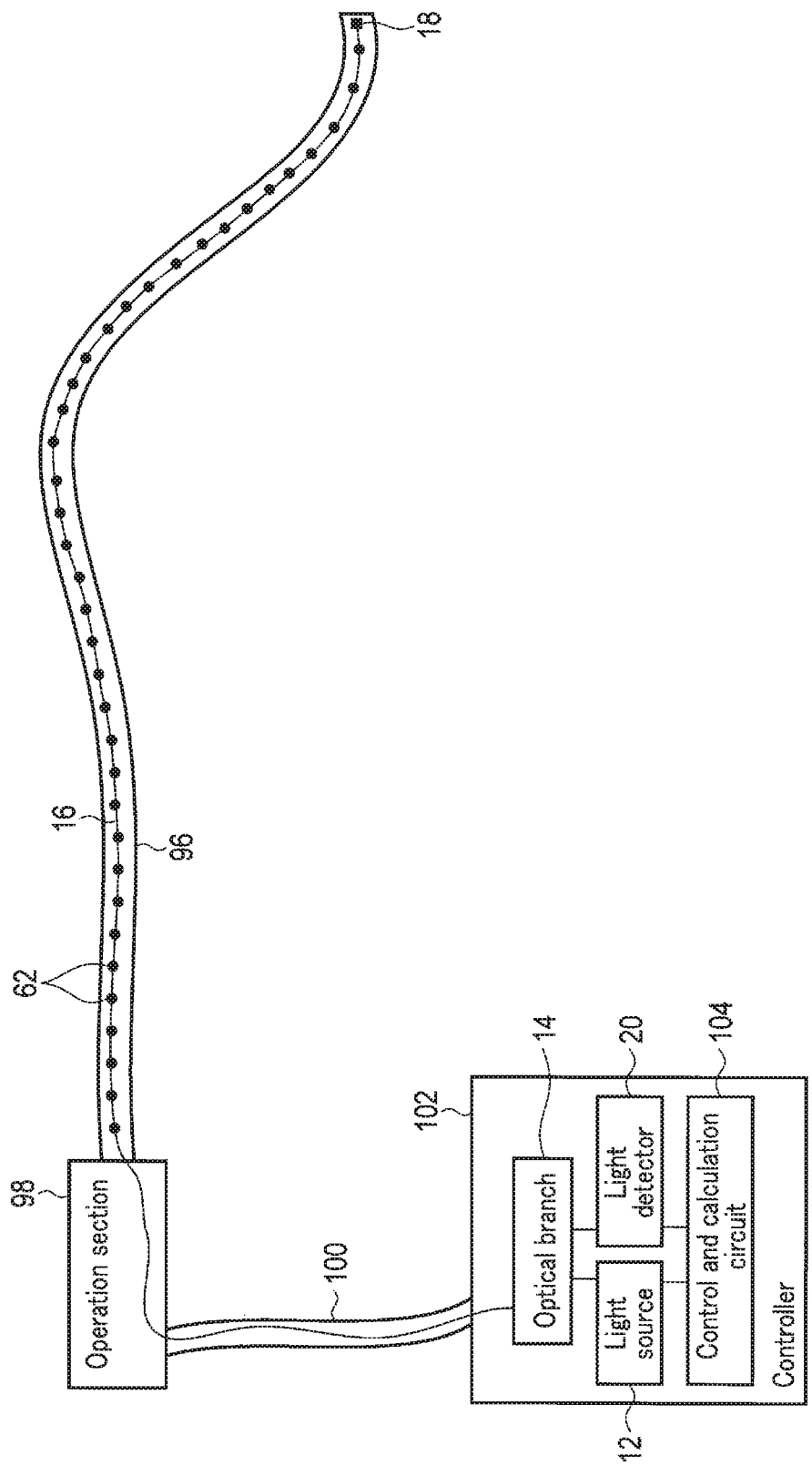
FIG. 20 is a block diagram showing a schematic configuration of an endoscope apparatus according to an embodiment of the present invention, which is equipped with a curvature sensor according to one embodiment.

For example, FIG. 20 shows an endoscope system in which the light guide 16 of the curvature sensor 10 according to the present embodiment is disposed along an insertion section 96 of an endoscope as a tubular insert. This endoscope system includes the endoscope provided with the elongated insertion section 96 which is the tubular insert to be inserted into a subject (e.g. a body cavity (lumen)) that is an observation target, an operation section 98 coupled to the proximal end of the insertion section 96, and a connection cable 100. The endoscope system further includes a controller 102 which controls the endoscope.

Here, the insertion section 96 has, from the distal-end side to the proximal-end side of the insertion section 96, a distal-end rigid portion, an operation bending portion which bends, and a flexible tubular portion. The distal-end rigid portion is the distal end of the insertion section 96, and is a rigid material. This distal-end rigid portion is provided with an unshown imaging device.

The operation bending portion bends in desired directions in response to an operation by an endoscope operator (a worker such as doctors) of a bending operation knob provided in the operation section 98. The operator bends the operation bending portion by operating the bending operation knob. The position and direction of the distal-end rigid portion are changed by the bending of this operation bending portion, and the observation target is caught in an observation field of view which is an imaging range of the imaging device. Illumination light is applied to the observation target that has been caught as above, from an unshown illumination window provided in the distal-end rigid portion, and the observation target is illuminated. The operation bending portion includes unshown node rings that are joined along the longitudinal direction of the insertion section 96. The node rings rotate relative to one another, and the operation bending portion bends accordingly.

The flexible tubular portion has desired flexibility, and is bent by external force. The flexible tubular portion is a tubular member extending from the operation section 98.

The connection cable 100 connects the operation section 98 and the controller 102 to each other.

The controller 102 subjects an observation image obtained by the imaging device of the endoscope to image processing, and displays the image-processed observation image on an unshown display device. In the present embodiment, as shown in FIG. 20, the light source 12, the optical branch 14, and the light detector 20 of the curvature sensor 10 are incorporated in this controller 102, and the optical fiber which is the light guide 16 is disposed to extend along the longitudinal axis direction of the insertion section 96 from this controller 102 through connection cable 100 and the operation section 98. The light reflector 18 is provided in the distal-end rigid portion of the insertion section 96. In this case, the sensing part groups 62 are provided at corresponding positions in the optical fiber and in the operation bending portion and the flexible tubular portion of the insertion section 96.

As described above, the sensing part groups 62 can independently measure the bending direction and bending amount (curvature information) of each part of the optical fiber. Therefore, if a large number of sensing part groups 62 enough for the degree of deformation of the operation bending portion and the flexible tubular portion of the insertion section 96 which are measurement targets are formed, it is possible to measure the bending amount and bending direction, that is, the curvature information of the insertion section 96.

The controller 102 further includes a control and computing circuit 104. This control and computing circuit 104 controls the light emission of the light source 12. Moreover, the control and computing circuit 104 can compute a three-dimensional shape of the insertion section 96 as the secondary information from the curvature information of the optical fiber, that is, the insertion section 96 measured by the light detector 20, and display the obtained three-dimensional shape on the unshown display device.

The tubular insert is not limited to this endoscope, and may be, for example, various probes, catheters, or over sheaths (tubes used to assist the insertion of endoscopes and catheters).

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A curvature sensor which detects curvature information from a plurality of optical signals derived from a plurality of sensing parts provided in a light guide having flexibility, the curvature sensor comprising:
a light source which generates sensor light in emission wavelength regions including at least predetermined wavelength components;
the light guide which has flexibility and confines and guides the sensor light;
the sensing parts formed in at least one of (i) different positions in a longitudinal direction of the light guide and (ii) different directions in a circumferential direction in substantially a same position in the longitudinal direction thereof, and made of an elastic material, each of the sensing parts being configured to include an optical characteristic changing member which generates the optical signals having absorption wavelength characteristic regions that vary from sensing part to sensing part by changing optical characteristics of the sensor light guided by the light guide in accordance with an amount of bending of the light guide; and
a light sensor which detects the optical signals included in the sensor light from the light source, which has passed through the sensing parts and undergone the optical characteristic change, wherein
the optical characteristic changing member is selected from a group consisting of a photoexcited plasmon generating material, a light absorbing material, a laminated dielectric film, a phosphor, and a grating structure,
the sensing parts use at least two different types of the optical characteristic changing member; and
the sensing parts have a refractive index that is larger than a refractive index of the light guide, and include a sensing part light confinement member having a refractive index that is smaller than the refractive index of the light guide to reflect light incident on the sensing parts from the light guide.

2. The curvature sensor according to claim 1, further comprising:
a curvature calculator which calculates the curvature information from the optical signals detected by the light sensor.

3. The curvature sensor according to claim 2, wherein the curvature calculator calculates curvature information of one of the sensing parts from the optical signals detected by the light sensor, with the sensing parts formed in different directions in a circumferential direction in substantially a same position in the longitudinal direction of the light guide, as one sensing part group.

4. The curvature sensor according to claim 2, wherein
in each of the different positions in the longitudinal direction of the light guide in which the sensing parts are formed, at least one sensing part is further formed in a different position in a circumferential direction in substantially a same position to make a sensing part group in each of the different positions in the longitudinal direction, and
the curvature calculator calculates curvature information of each of the sensing part groups from the optical signals detected by the light sensor.

5. The curvature sensor according to claim 1, wherein the photoexcited plasmon generating material of the optical characteristic changing member excites plasmon with light of at least one type of light source.

6. The curvature sensor according to claim 5, wherein the photoexcited plasmon generating material comprises one of at least one type of plasmonic substance, nanosized material, nanosized mineral, and nanosized metal.

7. The curvature sensor according to claim 5, wherein the photoexcited plasmon generating material comprises one of at least one type of plasmonic substance, nanosized material, nanosized minerals, and nanosized metal, which differ in at least one of the size, length and thickness of the sensing parts.

8. The curvature sensor according to claim 5, wherein the optical characteristic changing member is configured such that the photoexcited plasmon generating material is surrounded by one of a dispersant and a capsule.

9. The curvature sensor according to claim 1, wherein the light absorbing material absorbs light having at least overlapping wavelengths of at least one type of wavelength band by different absorption amounts in mutually different sensing parts.

10. The curvature sensor according to claim 9, wherein the light absorbing material is one of a dye and a pigment whose particles are nanosized.

11. The curvature sensor according to claim 9, wherein the optical characteristic changing member is configured such that the light absorbing material is surrounded by one of a dispersant and a capsule.

12. The curvature sensor according to claim 1, wherein the light sensor has detection wavelength bands, the number of which is equal to or larger than the number of sensing parts.

13. The curvature sensor according to claim 1, wherein the light source emits sensor light in the emission wavelength region, including one of at least a wavelength component of the absorption wavelength characteristic regions and at least part of the wavelength component of the absorption wavelength characteristic regions.

14. The curvature sensor according to claim 1, wherein the light source emits sensor light in the emission wavelength region having substantially uniform light intensity in all wavelength components of the absorption wavelength characteristic region.

15. The curvature sensor according to claim 1, wherein
the sensing parts further includes at least one of a narrow-band absorption member having absorption characteristics only in a short range of a wavelength band and a fluorescent member which absorbs predetermined light and generates a spectrum of another wavelength,
the light source is allowed to supply light of a wavelength necessary for the at least one of the narrow-band absorption member and the fluorescent member, and
the light sensor is allowed to detect a change of light by the at least one of the narrow-band absorption member and the fluorescent member.

16. The curvature sensor according to claim 1, wherein
the light source is composed of a plurality of discrete light sources, and
each of the discrete light sources emits light in a wavelength region which is part of a wavelength region within the emission wavelength region and which does not overlap other discrete light sources completely, so as not to overlap temporally with the other discrete light sources.

17. The curvature sensor according to claim 1, wherein the optical characteristic changing member is made of metal particles to absorb light in a predetermined wavelength region and has a special spectral absorption spectrum different from a spectral absorption spectrum peculiar to the metal, and
the sensing parts are provided with optical characteristic changing members having different special spectral absorption spectra, and the special spectral absorption spectra of all the optical characteristic changing members at least overlap the emission wavelength region of the sensor light from the light source.

18. An endoscope comprising:
an insertion section which is a tubular insert to be insert into a subject that is an observation target; and
the curvature sensor according to claim 1 in which the light guide is disposed along the insertion section.

19. A curvature sensor which detects curvature information from a plurality of optical signals derived from a plurality of sensing parts provided in a light guide having flexibility, the curvature sensor comprising:
a light source which generates sensor light in emission wavelength regions including at least predetermined wavelength components;
the light guide which has flexibility and confines and guides the sensor light;
the sensing parts formed in at least one of (i) different positions in a longitudinal direction of the light guide and (ii) different directions in a circumferential direction in substantially a same position in the longitudinal direction thereof, and made of an elastic material, each of the sensing parts being configured to include an optical characteristic changing member which generates the optical signals having absorption wavelength characteristic regions that vary from sensing part to sensing part by changing optical characteristics of the sensor light guided by the light guide in accordance with an amount of bending of the light guide; and
a light sensor which detects the optical signals included in the sensor light from the light source, which has passed through the sensing parts and undergone the optical characteristic change, wherein
the optical characteristic changing member is made of metal particles to absorb light in a predetermined wavelength region and has a special spectral absorption spectrum different from a spectral absorption spectrum peculiar to the metal,
the sensing parts are provided with optical characteristic changing members having different special spectral absorption spectra, and the special spectral absorption spectra of all the optical characteristic changing members at least overlap the emission wavelength region of the sensor light from the light source, and
the sensing parts have a refractive index that is larger than a refractive index of the light guide, and include a sensing part light confinement member having a refractive index that is smaller than the refractive index of the light guide to reflect light incident on the sensing parts from the light guide.

* * * * *